US012807564B2

(12) United States Patent
Dorok et al.

(10) Patent No.: US 12,807,564 B2
(45) Date of Patent: Nov. 24, 2026

(54) CERIUM-ETHYLENEDIAMINE KETONE-TYPE AND CERIUM-SALEN-TYPE COMPLEXES AND USE THEREOF IN ORGANIC ELECTRONICS

(71) Applicant: CREDOXYS GmbH, Dresden (DE)

(72) Inventors: Sascha Dorok, Dresden (DE); Marcus Papmeyer, Nossen (DE); Leonard Eymann, Dresden (DE); Julia Stolz, Dresden (DE)

(73) Assignee: CREDOXYS GMBH, Dresden (DE)

( * ) Notice: Subject to any disclaimer, the term of this patent is extended or adjusted under 35 U.S.C. 154(b) by 861 days.

(21) Appl. No.: 18/252,811

(22) PCT Filed: Nov. 11, 2021

(86) PCT No.: PCT/EP2021/081392

§ 371 (c)(1),
(2) Date: May 12, 2023

(87) PCT Pub. No.: WO2022/101343

PCT Pub. Date: May 19, 2022

(65) Prior Publication Data

US 2023/0422602 A1 Dec. 28, 2023

(30) Foreign Application Priority Data

Nov. 16, 2020 (DE) ..................... 10 2020 130 218.5

(51) Int. Cl.

| | |
|---|---|
| ***H10K 85/30*** | (2023.01) |
| ***C07C 251/12*** | (2006.01) |
| ***C07F 5/00*** | (2006.01) |
| ***H10K 50/14*** | (2023.01) |
| ***H10K 50/16*** | (2023.01) |
| ***H10K 50/17*** | (2023.01) |

(52) U.S. Cl.

CPC ............ *C07C 251/12* (2013.01); *C07F 5/003* (2013.01); *H10K 85/351* (2023.02); *H10K 50/14* (2023.02); *H10K 50/16* (2023.02); *H10K 50/17* (2023.02)

(58) Field of Classification Search

CPC ...... H10K 50/14; H10K 50/155; H10K 50/16; H10K 50/17; H10K 50/351; C07F 5/003

See application file for complete search history.

(56) References Cited

U.S. PATENT DOCUMENTS

| | | | |
|---|---|---|---|
| 2015/0295276 A1 | 10/2015 | Ishiji | |
| 2020/0270280 A1 * | 8/2020 | Niu ....................... | C07F 7/0814 |

FOREIGN PATENT DOCUMENTS

| | | |
|---|---|---|
| EP | 2180029 B1 | 7/2011 |
| WO | WO2000/32719 | 6/2000 |
| WO | WO2021048044 A1 | 3/2021 |

OTHER PUBLICATIONS

Balasubramanian, V., et al., Synthesis and Reactivity of Quadridentate Schiff Base Chelates of Lanthanide(III) Ions, Asian Journal of Chemistry, 15(1): 139-143, 2003.

Dutt, N., et al., Chemistry of Lanthanons—XIX, Ethylenediamine Bis-Acetylacetone Complexes of Rare-Earths, J Inorg Nucl Chem, 30: 3273-3280, 1968.

Schafer, J., et al., Fluorinated Cerium(IV) Enaminolates: Alternative Precursors for Chemical Vapor Deposition of CeO2 Thin Films, Inorganic Chemistry, 55: 5422-5429, 2016.

Timmons, J., et al., Template Synthesis and Crystal and Molecular Structure of Bis[1,1,1,12, 12, 12-hexafluoro-2, 11-bis(trifluoromethyl)-4,9-dimethyl-2, 11-diolato-5,8-diazadodeca-4,8-diene(2−)]cerium(IV), CeC2gH3F2,0,N, A Fluorinated Schiff Base Complex of Eight-Coordinate Cerium(IV), Inorganic Chemistry, 19(12): 3553-3557, Dec. 1980.

Wester, D., et al., Electrochemical Studies of Cerium Chelate Complexes, Inorganic Chemistry, 24: 4435-4437, 1985.

Afshar, Schiff Base Complexes of the Lanthanoids and Actinoids. Part 3. Lanthanoid(III), Cerium(IV), Thorium(IV), and Uranium(IV) Complexes with NN'-Ethylenebis(5t-butylsalicylideneimine); H N.M. R. and other Spectroscopic Properties, Inorganica Chimica Acta, 38: 145-149, 1980.

Baker, et al., Preparation and Properties of Some Hydrocarbon-Soluble Cerium and Iron Compounds, Journal of Chemical and Engineering Data, 7(2): 560-563, Oct. 1962.

Gottfriedsen, et al., Synthesis and Structure of the Cerium Schiff-Base Complexes [Ce(Salen)2] and [(THF)2KCe(Salen)2], Z. Anorg. Allg. Chem., 634: 514-518, 2008.

Hardy, E., et al., Th(IV) and Ce(IV) Napthylsalophen Sandwich Complexes: Characterization of Unusual Thorium Fluorescence in Solution and Solid-state, Chem. Commun., 53, 11984-11987, 2017.

* cited by examiner

*Primary Examiner* — Golam Mowla

(74) *Attorney, Agent, or Firm* — Weston R. Gould; DINSMORE & SHOHL LLP

(57) ABSTRACT

The present invention relates to an electronically doped semiconductor material and to an electronic component comprising cerium-ethylenediamine ketone-type and cerium-salen-type complexes. The invention also relates to the use of the cerium-ethylenediamine ketone-type and cerium-salen-type complexes as electron acceptors, especially as p-dopants and electron transport materials in organic-electronic components. The invention further relates to novel cerium-ethylenediamine ketone-type and cerium-salen-type complexes.

17 Claims, No Drawings

CERIUM-ETHYLENEDIAMINE KETONE-TYPE AND CERIUM-SALEN-TYPE COMPLEXES AND USE THEREOF IN ORGANIC ELECTRONICS

CROSS REFERENCE TO RELATED APPLICATIONS

This application is a U.S. National Stage under 35 U.S.C. § 371 of international patent application number PCT/EP2021/081392, which depends from and claims priority to German Application No: 10 2020 130 218.5 filed Nov. 16, 2020, the entire contents of each of which are incorporated herein by reference.

The present invention relates to an electronically doped semiconductor material and to an electronic component comprising cerium-ethylenediamine ketone-type and cerium-salen-type complexes. The invention also relates to the use of the cerium-ethylenediamine ketone-type and cerium-salen-type complexes as electron acceptors, especially as p-dopants and electron transport materials in organic-electronic components. The invention further relates to novel cerium-ethylenediamine ketone-type and cerium-salen-type complexes.

BACKGROUND OF THE INVENTION

Organic electronics focuses on the development, characterization and application of new materials, both based on small organic molecules and polymers with certain desired electronic properties for the production of electronic components. These comprise e.g. organic field effect transistors (OFETs) such as organic thin film transistors (OTFTs), organic electroluminescent devices such as organic light emitting diodes (OLEDs), organic solar cells (OSCs), e.g. exciton solar cells, dye-sensitized solar cells (DSSCs) or perovskite solar cells, electrophotography, e.g. photoconductive materials in organic photoconductors (OPCs), organic optical detectors, organic photoreceptors, light-emitting electrochemical cells (LECs) and organic laser diodes.

It is known that organic semiconductor matrices can be heavily influenced regarding their electrical conductivity by doping. Such organic semiconductive matrix materials can be formed by either from compounds with good electron donor properties (p-conductor) or from compounds with good electron acceptor properties (n-conductor). In contrast to inorganic semiconductors, organic semiconductors have a very low intrinsic charge carrier concentration. Organic semiconductor matrix materials are therefore usually doped in order to achieve good semiconductor properties. For n-doping strong electron donors (n dopants) are used, which transfer an electron to the LUMO of the semiconductor matrix (n-doping), resulting in a free electron on the matrix (SOMO). For p-doping strong electron acceptors (p-dopants) are used, which remove an electron from the HOMO of the semiconductor matrix (p-doping), resulting in a hole. In other words, for p-doping the LUMO of the dopant must be below the HOMO-energy of the matrix. The dopant acts as an acceptor and leaves a mobile hole (SOMO) in the matrix.

Known p-dopants for electron donor materials are electron acceptors such as tetracyanoquinone methane (TCNQ), 2,3,5,6-tetrafluorotetracyano-1,4-benzoquinone methane (F4TCNQ), trinaphthylenes (HATNA), metal oxides such as $MoO_3$ or $WO_3$, or radialene compounds as e.g., described in EP 2180029. The acceptor molecules generate so-called holes in the semiconductor matrix materials (hole transport materials) by electron transfer processes and the conductivity of the semiconductor matrix material (hole transport material) is more or less changed depending on the number and mobility of the holes.

However, the previously described compounds or compound classes have disadvantages for a technical use in the production of doped semiconductors or of corresponding electronic components with such doped layers. The compounds or compound classes mentioned are, for example, too volatile, have a too high absorption coefficient, have an unstable evaporation rate and/or show low thermostability. In addition, some of these compounds have very high production costs.

Thus, there is still a demand for compounds, which are easily available or producible, are suitable for doping electron donor materials and do not have the disadvantages described above.

Only a few cerium ethylenediamine ketone-type complexes and no cerium salen-type (cerium bis(salicylidene) ethylenediamine-type) complexes are known. A few complexes of cerium-(IV) are described in the literature. J. Schläfer et al, Inorg. Chem, 2016, 55, 5422-5429 describes homopleptic cerium(IV) complexes that have the following ligands: N,N'-bis(4,4,4,-trifluorobut-1-en-3-one)-ethylenediamine, N,N'-bis(4,4,5,5-pentafluoropent-1-en-3-one)-ethylenediamine, N, N'-bis(4,4,5,5,6,6-heptafluorohex-1-en-3-one)-ethylenediamine and N,N'-bis(4,4,4,-trifluorobut-1-en-3-one)-propylenediamine.

In D. W. Wester et. al, Inorg, Chem. 1985, 24, 4435-4437, the following homopleptic cerium(IV) complexes are described:

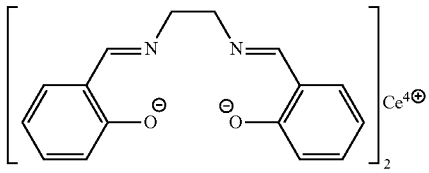

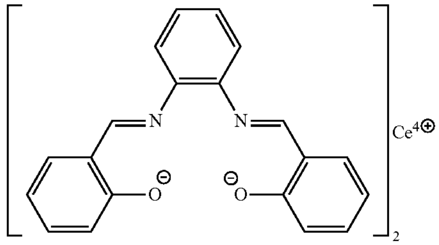

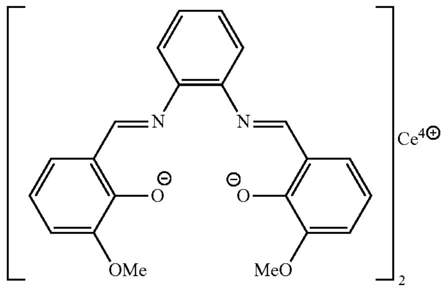

-continued

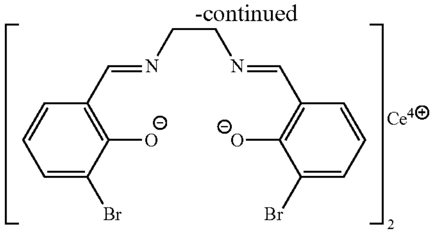

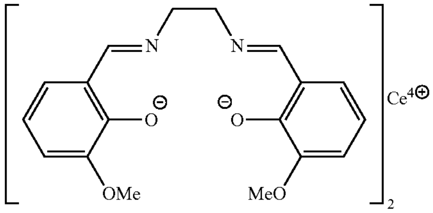

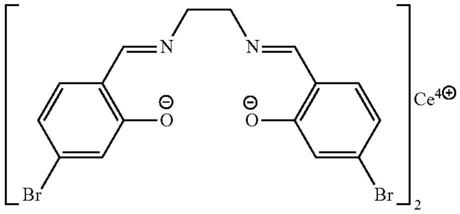

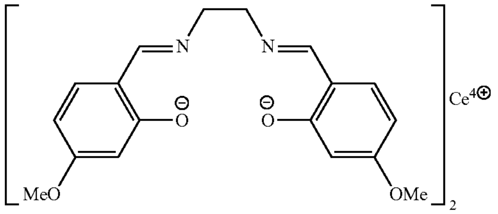

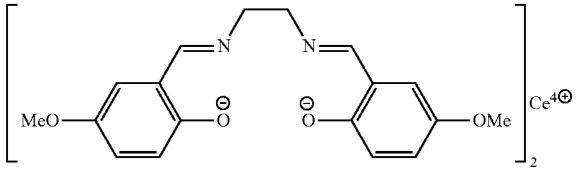

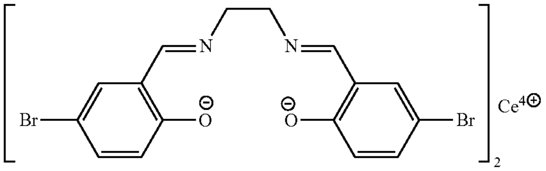

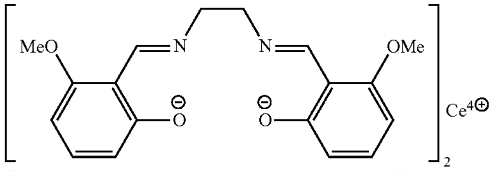

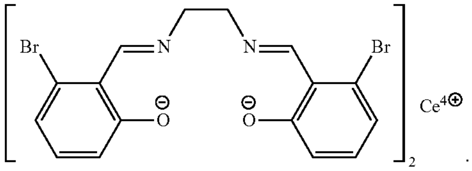

.

N. K. Dutt et al., (Chemistry of Lanthanons-XIX Ethylenediamine bis-Acetylacetone Complexes of Rare-Earths, J. Inorg. Nucl. Chem., 1968, Vol. 30, pp. 3273-3280) describes the synthesis of ethylenediamine bis-acetylacetone complexes of rare earths. Among other Ce(III) complexes are mentioned, [Ce(ethylenediamine-bis-aceylacetone)$Cl_3$] and [Ce(ethylenediamine-bis-acetylacetone)$NO_3$]. In these complexes, the ligand is neutral and thus carries no charge. According to the invention, the ligand is twice negatively charged.

V. Balasubramanian et al. (Synthesis and Reactivity of Quadridentate Schiff Base Chelates of Lanthanide(III) Ions, Asian Journal of Chemistry 2003, Vol. 15, No. 1, pp. 139-143) describes the synthesis of lathanide (III) chelate complexes. Ce(III) complexes mentioned include, [Ce(ethylenediamine-bis-acytylacetone)$Cl_3$] and [Ce(ethylenediamine-bis-acytylacetone-α-naphtylisocyanate))$Cl_3$], where ethylenediamine-bis-acytylacetone ligand is in the keto form. In these complexes, the ligand is neutral and thus carries no charge. According to the invention, the ligand is twice negatively charged.

J. H. Timmons (Template Synthesis and Crystal and Molecular Structure of Bis[1,1,1,12,12,12-hexafluoro-2,11-bis(trifluoromethyl)-4,9-dimethyl-2,11-diolato-5,8-diazadodeca-4,8-diene(2-)]cerium(IV), $CeC_{28}H_{28}F_{24}O_4N_4$, a fluorinated schiff base complex of eight-coordinate cerium (IV), Inorg. Chem. 1980, Vol. 19, No. 12, p. 3553-3557) describes a cerium (IV) complex. The ligand of this complex has a different connectivity of the atoms. In other words, the ligand is not based on an acetylacetone structure.

WO 2021/048044 describes cerium (IV) diketonate complexes as electron acceptors, specifically as p-dotands and electron transport materials that can be used in organic electronic devices.

Until now, it has been unknown to use cerium (IV) ethylenediamine ketone-type and/or cerium (IV) salen-type and/or cerium (IV) bis(salicylidene)ethylenediamine-type complexes (hereinafter referred also to as cerium (IV) complexes) in organic semiconductor materials. In particular, it has not yet been described to use such cerium (IV) complexes as p-dopants, as electron transport materials or as electron acceptors.

Surprisingly, it has now been found that cerium (IV) complexes can be advantageously used as p-dopants. Furthermore, it has been found that cerium (IV) complexes can be used as electron transport materials (ETM) in organic electronic components such as organic light emitting diodes (OLED), photovoltaic cells, organic solar cells (OPV), organic diodes or organic transistors.

Furthermore, many cerium (IV) diketonates can be evaporated very well under vacuum and occasionally exhibit high thermostability. Thus, they are basically suitable for both variants of processing of organic-electronic components, the vacuum coating (vapour deposition) and the solvent-based processing (solution processing).

SUMMARY OF THE INVENTION

A first object of the invention is an electronic component comprising at least one compound of general formula (I)

$$Ce^{4+}[L_1L_2]^{4-} \quad (I),$$

wherein $L_1$ and $L_2$ are each a tetradentate ligand independently selected from ligands of formula (I.1)

(I.1)

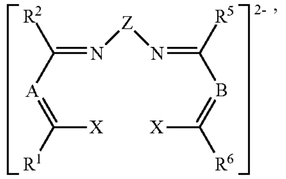

wherein

X independently from each other represents O or S;

Z is a bridging group, which has 2 or 3 carbon atoms between the nitrogen atoms, wherein the carbon atoms each being unsubstituted or substituted by 1, 2, 3, 4, 5 or 6 identical or different radicals $R^{12}$, wherein two adjacent carbon atoms may be linked to one another by a double bond, or 2 or 3 of the carbon atoms are part of a mononuclear, 2-nuclear or 3-nuclear $C_6$-$C_{14}$ aromatic or heteroaromatic ring system, wherein the heteroaromatic ring system has 4 to 13 carbon atoms and has 1, 2 or 3 identical or different heteroatoms or heteroatom-containing groups as ring members selected from N, $NR^8$, O, S, SO and $SO_2$ and wherein the aromatic or heteroaromatic ring system is unsubstituted or substituted by 1, 2, 3, 4 or 5 identical or different radicals $R^9$;

A and B independently from each other represent N or $CR^7$;

$R^1$ and $R^6$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_3$-$C_7$-cycloalkyl, wherein $C_3$-$C_7$-cycloalkyl is unsubstituted or substituted by 1, 2, 3, 4, 5 or 6 identical or different radicals $R^{11}$, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$; or $R^1$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^6$ und B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^2$ und $R^5$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_3$-$C_7$-cycloalkyl, wherein $C_3$-$C_7$-cycloalkyl is unsubstituted or substituted by 1, 2, 3, 4, 5 or 6 identical or different radicals $R^{11}$, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

$R^2$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^5$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^{4a}R^{4b}$ are independently from each other selected from hydrogen, $C_1$-$C_6$ alkyl and $C_6$ $C_{14}$ aryl, wherein aryl is unsubstituted or substituted with 1, 2, 3, 4 or 5 identical or different radicals $R^{10}$;

$R^7$ is selected from hydrogen, CN, nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl has 1, 2 or 3 identical or different heteroatoms or heteroatom-containing groups as ring members selected from N, $NR^8$, O, S, SO and $SO_2$, wherein aryl and hetaryl are unsubstituted or substituted with 1, 2, 3, 4 or 5 identical or different radicals $R^{10}$;

$R^8$ is selected from hydrogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl;

$R^{10}$ is selected from CN, halogen, $C_1$-$C_4$ alkyl, $C_1$-$C_4$ haloalkyl;

$R^{11}$ is selected from CN, halogen, $C_1$-$C_4$ alkyl, $C_1$-$C_4$ haloalkyl;

$R^{12}$ independently selected from halogen, CN, $C_1$-$C_6$-alkyl, $C_1$-$C_6$-haloalkyl, $C_1$-$C_6$-alkoxy, $C_1$-$C_6$-haloalkoxy, $C_3$-$C_7$-cycloalkyl, where $C_3$-$C_7$-cycloalkyl is unsubstituted or substituted by 1, 2, 3, 4, 5 or 6 identical or different radicals $R^{11}$, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$.

A further object of the invention is an electronic component comprising at least one compound of the general formula (I)

$$Ce^{4+}[L_1L_2]^{4-} \quad (I),$$

wherein $L_1$ and $L_2$ are each a tetradentate ligand independently selected from ligands of formula (II)

(II)

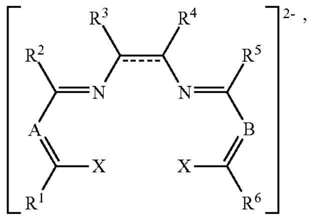

wherein

------ between the group $CR^3$-$CR^4$ represents a single or double bond;

X independently from each other represents O or S;

A and B independently from each other represent N or $CR^7$;

$R^1$ and $R^6$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$; or $R^1$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^6$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^3$ and $R^4$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$, or $R^3$ and $R^4$ together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^2$ and $R^5$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

$R^{4a}R^{4b}$ are independently from each other selected from hydrogen, $C_1$-$C_6$ alkyl and $C_6$ $C_{14}$ aryl, wherein aryl is unsubstituted or substituted with 1, 2, 3, 4 or 5 identical or different radicals $R^{10}$;

$R^7$ is selected from hydrogen, CN, nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl has 1, 2 or 3 identical or different heteroatoms or heteroatom-containing groups as ring members selected from N, $NR^8$, O, S, SO and $SO_2$, wherein aryl and hetaryl are unsubstituted or substituted with 1, 2, 3, 4 or 5 identical or different radicals $R^{10}$;

$R^8$ is selected from hydrogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl;

$R^{10}$ is selected from CN, halogen, $C_1$-$C_4$ alkyl, $C_1$-$C_4$ haloalkyl.

A further object of the invention is a doped semiconductor matrix material comprising at least one electron donor and at least one compound of formula (I) wherein $L_1$ and $L_2$ are each a tetradentate ligand independently selected from ligands of formula (I.1) or formula (II), wherein X, Z, A, B, $R^1$, $R^2$, $R^3$, $R^4$, $R^5$ and $R^6$ are as defined above and below.

A further object of the invention is the use of a compound of formula (I), wherein $L_1$ and $L_2$ are each a tetradentate ligand independently selected from ligands of formula (I.1) or formula (II), wherein X, Z, A, B, $R^1$, $R^2$, $R^3$, $R^4$, $R^5$ and $R^6$ are as defined above and below, as organic semiconductor, as doping agent in organic semiconductor matrix materials, especially as p-dopant in hole transport layers, as charge injector in a charge injection layer, as electronic transport layer, as cathode material in organic batteries, as electrochromic material, as electron acceptor.

A further object of the invention is the use of Ce(III)-complex anions obtained by reduction of a compound(I) as defined above and below or of charge transfer complexes of a compound (I), as defined above and below, with electron donors as organic conductor, in particular as an organic conductor, an electrochromic material, a charge-transfer complex or a ferromagnet.

A further object of the invention is a compound of general formula (I)

$$Ce^{4+}[L_1L_2]^{4-} \quad (I),$$

their charge transfer complexes, their reduction products and mixtures thereof, wherein $L_1$ and $L_2$ are each a tetradentate ligand independently selected from ligands of formula (I.1)

(I.1)

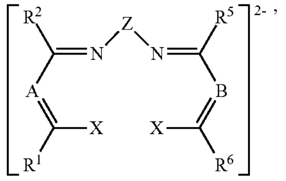

wherein

X independently from each other represents O or S;

Z is a bridging group, which has 2 or 3 carbon atoms between the nitrogen atoms, wherein the carbon atoms each being unsubstituted or substituted by 1, 2, 3, 4, 5 or 6 identical or different radicals $R^{12}$, wherein two adjacent carbon atoms may be linked to one another by a double bond, or 2 or 3 of the carbon atoms are part of a mononuclear, 2-nuclear or 3-nuclear $C_6$-$C_{14}$ aromatic or heteroaromatic ring system, wherein the heteroaromatic ring system has 4 to 13 carbon atoms and has 1, 2 or 3 identical or different heteroatoms or heteroatom-containing groups as ring members selected from N, $NR^8$, O, S, SO and $SO_2$ and wherein the aromatic or heteroaromatic ring system is unsubstituted or substituted by 1, 2, 3, 4 or 5 identical or different radicals $R^9$;

A and B independently from each other represent N or $CR^7$;

$R^1$ and $R^6$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_3$-$C_7$-cycloalkyl, wherein $C_3$-$C_7$-cycloalkyl is unsubstituted or substituted by 1, 2, 3, 4, 5 or 6 identical or different radicals $R^{11}$, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$; or $R^1$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^6$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^2$ and $R^5$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_3$-$C_7$-cycloalkyl, wherein $C_3$-$C_7$-cycloalkyl is unsubstituted or substituted by 1, 2, 3, 4, 5 or 6 identical or different radicals $R^{11}$, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

$R^2$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^5$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^{4a}R^{4b}$ are independently from each other selected from hydrogen, $C_1$-$C_6$ alkyl and $C_6$ $C_{14}$ aryl, wherein aryl is unsubstituted or substituted with 1, 2, 3, 4 or 5 identical or different radicals $R^{10}$;

$R^7$ is selected from hydrogen, CN, nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl has 1, 2 or 3 identical or different heteroatoms or heteroatom-containing groups as ring members selected from N, $NR^8$, O, S, SO and $SO_2$, wherein aryl and hetaryl are unsubstituted or substituted with 1, 2, 3, 4 or 5 identical or different radicals $R^{10}$;

$R^8$ is selected from hydrogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl;

$R^{10}$ is selected from CN, halogen, $C_1$-$C_4$ alkyl, $C_1$-$C_4$ haloalkyl;

$R^{11}$ is selected from CN, halogen, $C_1$-$C_4$ alkyl, $C_1$-$C_4$ haloalkyl;

$R^{12}$ independently selected from halogen, CN, $C_1$-$C_6$-alkyl, $C_1$-$C_6$-haloalkyl, $C_1$-$C_6$-alkoxy, $C_1$-$C_6$-haloalkoxy, $C_3$-$C_7$-cycloalkyl, where $C_3$-$C_7$-cycloalkyl is unsubstituted or substituted by 1, 2, 3, 4, 5 or 6 identical or different radicals $R^{11}$, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

with the proviso that the following compounds are excluded:

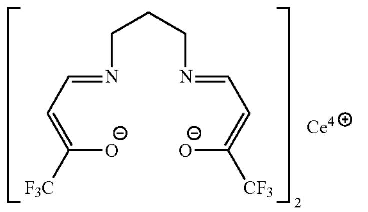

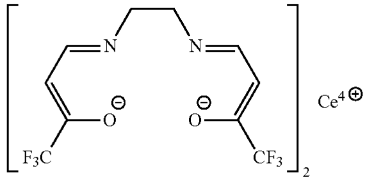

-continued

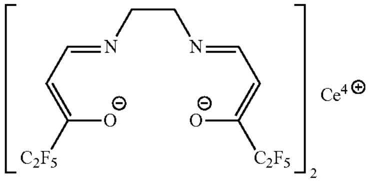

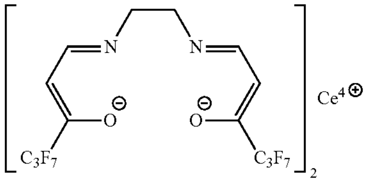

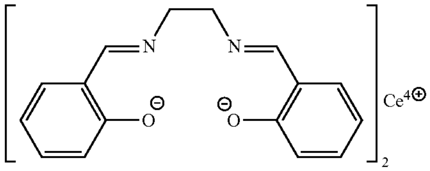

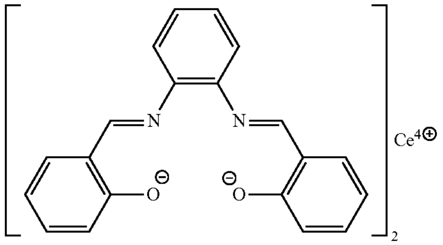

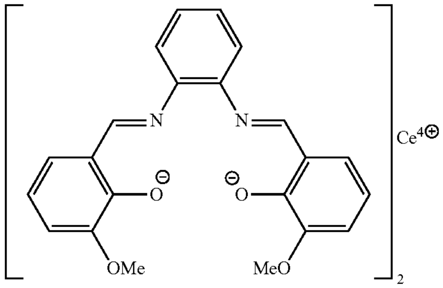

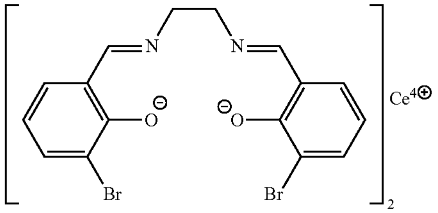

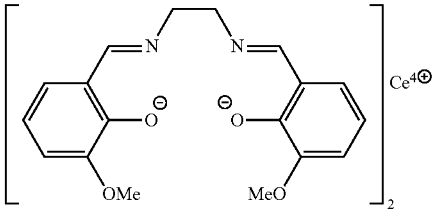

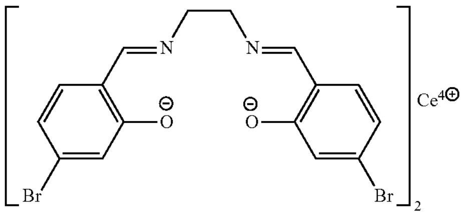

-continued

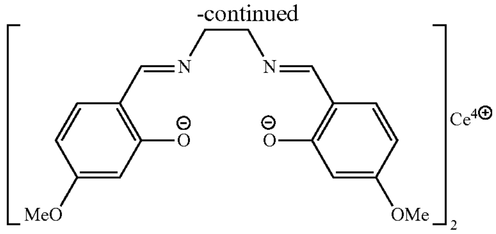

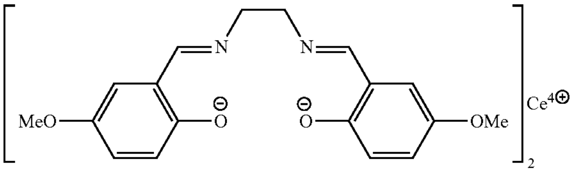

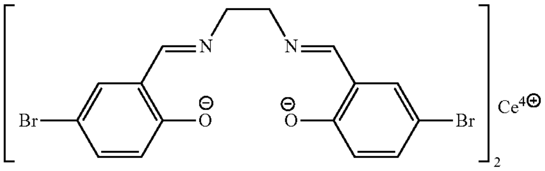

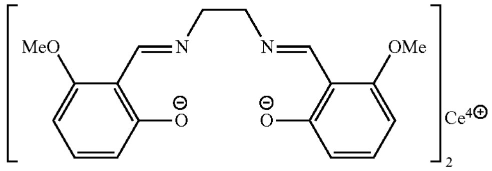

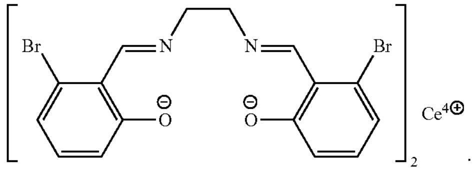

.

A further object of the invention are compounds of general (I)

$$Ce^{4+}[L_1L_2]^{4-} \quad (I),$$

their charge transfer complexes, their reduction products and mixtures thereof, wherein $L_1$ and $L_2$ are each a tetradentate ligand independently selected from ligands of formula (II)

(II)

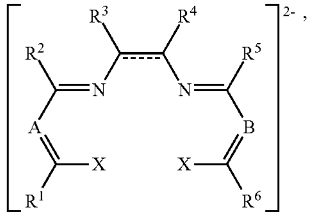

wherein $\overline{\phantom{--}}$ between the group $CR^3$-$CR^4$ represents a single or double bond;

X independently from each other represents O or S;

A and B independently from each other represent N or $CR^7$;

$R^1$ and $R^6$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$; or $R^1$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^6$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^3$ and $R^4$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$, or $R^3$ and $R^4$ together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^2$ and $R^5$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

$R^{4a}R^{4b}$ are independently from each other selected from hydrogen, $C_1$-$C_6$ alkyl and $C_6$ $C_{14}$ aryl, wherein aryl is unsubstituted or substituted with 1, 2, 3, 4 or 5 identical or different radicals $R^{10}$;

$R^7$ is selected from hydrogen, CN, nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl has 1, 2 or 3 identical or different heteroatoms or heteroatom-containing groups as ring members selected from N, $NR^8$, O, S, SO and $SO_2$, wherein aryl and hetaryl are unsubstituted or substituted with 1, 2, 3, 4 or 5 identical or different radicals $R^{10}$;

$R^8$ is selected from hydrogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl;

$R^{10}$ is selected from CN, halogen, $C_1$-$C_4$ alkyl, $C_1$-$C_4$ haloalkyl, with the proviso that the following compounds and their reaction products of formula (I) are excluded:

$L_1$=$L_2$=N,N'-bis(4,4,4,-trifluorobut-1-en-3-one)-ethylendiamine, $L_1$=$L_2$=N,N'-bis(4,4,5,5,5-pentafluoropent-1-en-3-one)-ethylendiamine, $L_1$=$L_2$=N,N'-bis(4,4,5,5,6,6,6-heptafluorohex-1-en-3-one)-ethylendiamine and the following compounds and their reaction products:

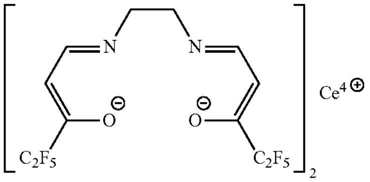

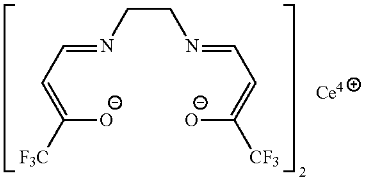

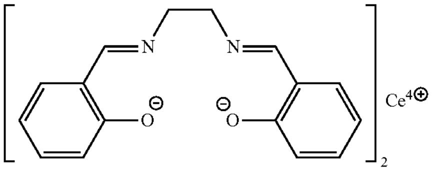

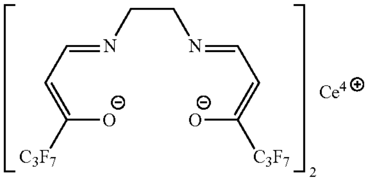

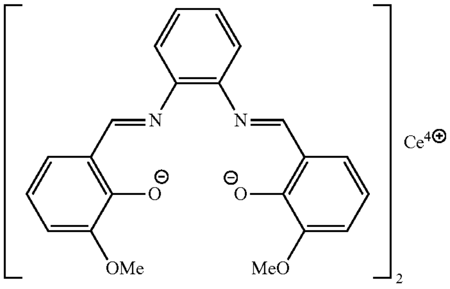

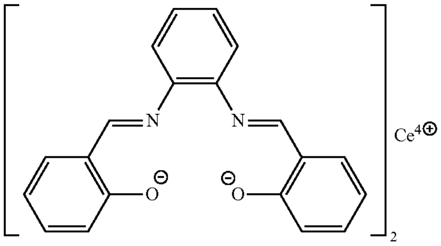

-continued

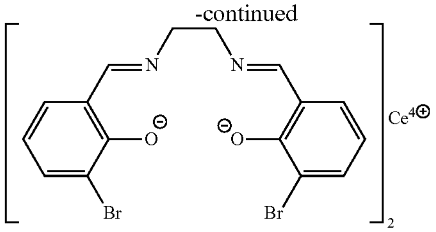

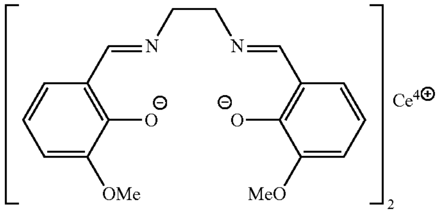

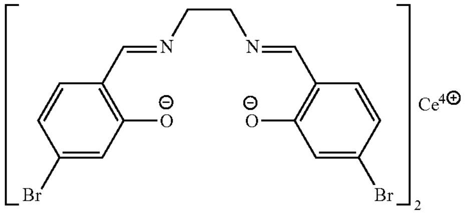

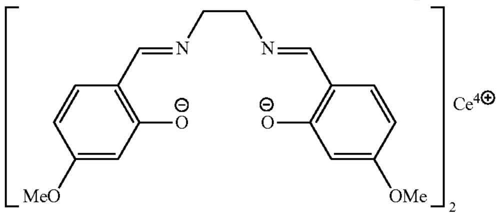

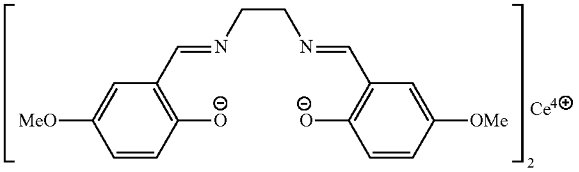

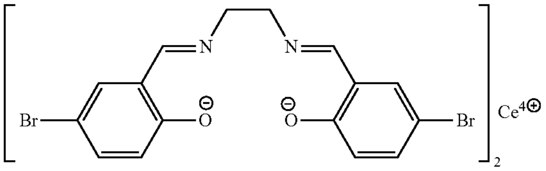

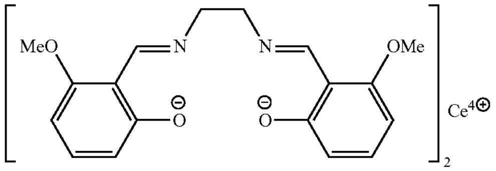

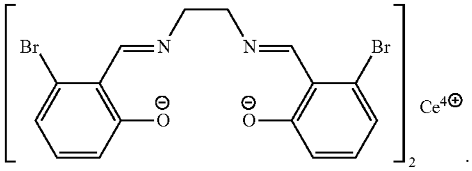

.

The invention has the following advantages:

The cerium-(IV)-complexes according to the invention have only low production costs.

The cerium-(IV)-complexes according to the invention are advantageously suitable as electron acceptors for use as p-dopants and as electron transport materials in organic-electronic components.

The cerium-(IV)-complexes according to the invention exhibit better conductivity compared to known electron acceptors.

The cerium-(IV)-complexes according to the invention show an improved thermostability of the doped layers compared to the state of the art.

Furthermore, the cerium (IV) complexes according to the invention are characterized by a higher doping efficiency.

The cerium-(IV)-complexes according to the invention show only a low absorption of the doped layer. Therefore, parasitic absorption and emissions can be reduced or even prevented.

The cerium-(IV)-complexes according to the invention are suitable for the production of organic and hybrid opto-electronic components, both by means of solvent processing and by vacuum reprocessing.

The terms cerium compound and cerium complex are used synonymously and are defined by formula (I). The ligands in the absence of the metal atom (cerium atom), are defined by the formula (II).

The term reduction products of a compound (I) are anion complexes, in particular Ce(III) anion complexes, where the corresponding counterion is donated from the hole conductive material (HTL) of the matrix. Semiconductor matrix materials are defined below.

In the sense of the invention, $[Ce(ac_2en)Cl_3]$, $[Ce(enac)_2 Cl_3]$ and $[Ce(enac)_2 (NO_3)_3]$ are not reduction products of compound (I), where $ac_2en$ and enac have the same meanings and in particular $ac_2en$ is bis(acetylacetone)ethylenediamine in the keto form and enac is ethylenediamine-bis-acetylacetone.

The term charge transfer complexes of a compound (I) refers to its ionic pairings with the radical cations of the matrix material (hole transport material, HTL).

In the context of the invention, formula (II) represents an exemplary mesomeric structure to which the ligands $L_1$ and $L_2$ are not restricted. Other mesomeric structures are selected from formula a, b, c and d

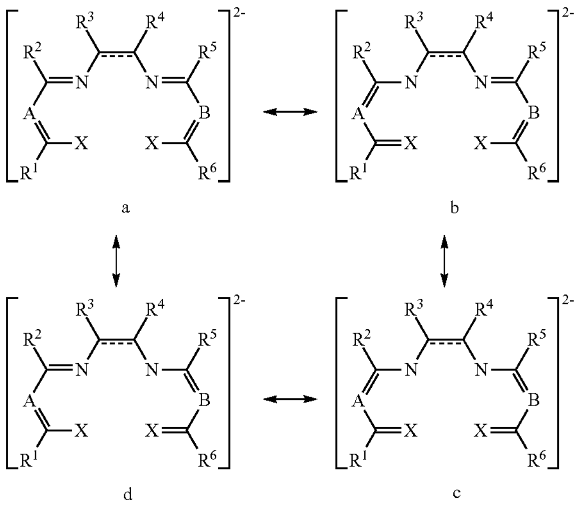

The mesomeric structures a, b, c, and d apply analogously to the ligands of formula (I.1).

Preferably, $L_1$ and $L_2$ have the mesomeric structure of formula a.

In the context of the invention, a tetradentate ligand (also called a tetradentate) is a ligand that binds to the metal atom (cerium atom) with four atoms.

In the context of the invention, a homoleptic cerium(IV) compound is a complex in which all ligands are identical ($L_1=L_2$).

In the context of the invention, a heteroleptic cerium(IV) compound is a complex in which one ligand has a different meaning than the other ligand ($L_1 \neq L_2$).

In the context of the invention, the prefix $C_n$-$C_m$ indicates the number of carbon atoms that a molecule or residue designated thereby may contain.

In the context of the invention, the expression "$C_1$-$C_6$-alkyl" refers to unbranched or branched saturated hydrocarbon groups having 1 to 6 carbon atoms. $C_1$-$C_6$-alkyl are e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl. $C_1$-$C_4$-alkyl refers, e.g., to methyl, ethyl, propyl, 1-methylethyl, butyl, 1-methylpropyl, 2-methylpropyl or 1,1-dimethylethyl.

In the context of the invention the expression "$C_1$-$C_6$-alkoxy" refers to an unbranched or branched saturated $C_1$-$C_6$-alkyl group as defined above, which is bound via an oxygen atom. Alkoxy radicals with 1 to 4 carbon atoms are preferred, particularly preferred are 1 or 2 carbon atoms. $C_1$-$C_2$-alkoxy is methoxy or ethoxy. $C_1$-$C_4$-alkoxy is e.g., methoxy, ethoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-alkoxy comprises the meanings given for $C_1$-$C_4$-alkoxy and additionally e.g., pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexyloxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy and 3,3-dimethylbutoxy.

In the context of the invention the expression "$C_1$-$C_6$-alkylsulfanyl" refers to an unbranched or branched saturated $C_1$-$C_6$-alkyl group as defined above, which is bound via a sulfur atom. Alkylsulfanyl radicals with 1 to 4 carbon atoms are preferred, particularly preferred are 1 or 2 carbon atoms. $C_1$-$C_2$-alkylsulfanyl is methylsulfanyl or ethylsulfanyl. $C_1$-$C_4$-alkylsulfanyl is e.g., methylsulfanyl, ethylsulfanyl, n-propylsulfanyl, 1-methylethylsulfanyl (isopropylsulfanyl), butylsulfanyl, 1-methylpropylsulfanyl (sec-butylsulfanyl), 2-methylpropylsulfanyl (isobutylsulfanyl) or 1,1-dimethylethylsulfanyl (tert-butylsulfanyl). $C_1$-$C_6$-alkylthio comprises the meanings given for $C_1$-$C_4$-alkylsulfanyl and additionally also, e.g., pentylsulfanyl, 1-methylbutylsulfanyl, 2-methylbutylsulfanyl, 3-methylbutylsulfanyl, 1,1-dimethylpropylsulfanyl, 1,2-dimethylpropylsulfanyl, 2,2-dimethylpropylsulfanyl, 1-ethylpropylsulfanyl, hexylsulfanyl, 1-methylpentylsulfanyl, 2-methylpentylsulfanyl, 3-methylpentylsulfanyl, 4-methylpentylsulfanyl, 1,1-dimethylbutylsulfanyl, 1,2-dimethylbutylsulfanyl, 1,3-dimethylbutylsulfanyl, 2,2-dimethylbutylsulfanyl, 2,3-dimethylbutylsulfanyl, 3,3-dimethylbutylsulfanyl, 1-ethylbutylsulfanyl, 2-ethylbutylsulfanyl, 1,1,2-trimethylpropylsulfanyl, 1,2,2-trimethylpropylsulfanyl, 1-ethyl-1-methylpropylsulfanyl or 1-ethyl-2-methylpropylsulfanyl.

In the context of the invention the expressions "haloalkyl", "haloalkoxy" and "haloalkyl-sulfanyl" refer to partially or fully halogenated alkyl, alkoxy or alkylsulfanyl. In other words, one or more hydrogen atoms, for example 1, 2, 3, 4 or 5 hydrogen atoms bonded to one or more carbon atoms of alkyl, alkoxy or alkylsulfanyl are replaced by a halogen atom, in particular by fluorine or chlorine.

In the context of the invention, the term "cycloalkyl" refers to carbocyclic, monocyclic radicals with 3 to 7 carbons, such as cyclopropyl, cyclobutyl, cyclopentyl, cyclohexyl, cycloheptyl; preferred are cyclopentyl, cyclohexyl and cycloheptyl, wherein the linkage to the radical of the molecule can take place via any suitable C atom. In the case of substitution, these may generally bear 1, 2, 3, 4, 4, 5 or 6, preferably 1, 2 or 3 and particularly preferably 1 "substituent" as defined above In the context of the invention, the term "alkylene" refers to an alkanediyl group, i.e. hydrocarbon bridging groups with 2 or 3 carbon atoms, such as $-(CH_2)_2-$, $-(CH_2)_3-$, $-CH_2-CH-CH_2-$. In the case of substitution, these can generally carry 1, 2 or, 3 substituents $R^{12}$ as defined above.

In the context of the invention, the term "alkenylene" refers to the mono- or poly-unsaturated, in particular monounsaturated analogues of the alkylene groups with 2 or 3 carbon atoms, such as $-CH=CH-$, $-CH=CH-CH_2-$, $-CH_2-CH=CH-$. In the case of substitution, these can generally carry 1, 2 or, 3 substituents $R^{12}$ as defined above.

In the context of the invention, the term "part of a 1-nuclear, 2-nuclear or 3-nuclear $C_6$-$C_{14}$ aromatic or heteroaromatic ring system" refers to the corresponding twice or multiply linked analogues of the aryls or hetaryls.

In the context of the invention, the expression "bridging group having 2 or 3 carbon atoms between nitrogen atoms" corresponds to having 2 or 3 carbon atoms in direct line between the flanking bonds (nitrogen atoms).

The expression "halogen" denotes in each case fluorine, chlorine, bromine or iodine.

The expression "aryl" comprises in the context of the invention mono- or polynuclear aromatic hydrocarbon radicals with usually 6 to 14, preferably 6 to 10 carbon atoms. Examples of aryl are in particular phenyl, naphthyl, indenyl, fluorenyl, anthracenyl, phenanthrenyl, naphthacenyl, chrysenyl, pyrenyl, etc. and especially phenyl or naphthyl.

The expression "hetaryl" comprises in the context of the invention mono- or poly-nuclear aromatic hydrocarbon radicals with 4 to 13 carbon atoms, wherein 1, 2 or 3 carbon atoms have been replaced by 1, 2 or 3 identical or different heteroatoms or heteroatom-containing groups as ring members, said heteroatoms and heteroatom-containing groups, selected from N, $NR^8$, O, S, SO and $SO_2$. The hetaryl group may be attached to the remainder of the molecule via a ring carbon or via a ring nitrogen. Examples of 5- or 6-membered aromatic heterocyclic rings (also called heteroaromatic rings or hetaryl) are 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl. Examples of 8-, 9- or 10-membered aromatic heterobicyclic rings are hetaryl having one of the aforementioned 5- or 6-membered heteroaromatic rings and another aromatic carbocycle or 5- or 6-membered heterocycle fused thereto, for example a fused benzene, thiophen-, furan-, pyrrol-, pyrazol-, imidazol-, pyridin- or pyrimidinring. These bicyclic hetarylenes comprises e.g. quinolinyl, isoquinolinyl, cinnolinyl, indolyl, indolizinyl, isoindolyl, indazolyl, benzofuryl, in particular 2-benzofuryl, benzothienyl, in particular 2-benzothienyl, benzo[b]thiazolyl, in particular 2-benzo[b]thiazolyl, benzoxazolyl, in particular 2-benzoxazolyl, benzothiazolyl, in particular 2-benzothiazolyl, benzimidazolyl, in particular 2-benzimidazolyl, imidazo[1,2-a]pyridin-2-yl, thieno[3,2-b]pyridin-5yl, imidazo-[2,1-b]-thiazol-6-yl and 1,2,4-triazolo[1,5-a]pyridin-2-yl.

The expression "CN" denotes the cyano group (—C≡N).

When # appears in a formula, showing a preferred substructure of a compound of the present invention, it denotes the bond to the rest of the molecule.

Cerium Compounds of the Formula (I)

Suitable cerium(IV) compounds in the sense of the invention are compounds of the general formula (I)

$$Ce^{4+}[L_1L_2]^{4-} \quad (I),$$

wherein $L_1$ and $L_2$ has one of the meanings as defined above and below, wherein

- $L_1$ and $L_2$ have the same meaning,
- $L_1$ and $L_2$ each having different meanings, and
- mixtures of two or more compounds of formula (I).

Preferred are compounds of formula (I), wherein $L_1$ and $L_2$ have the same meanings.

The homoleptic compounds of formula (I) are prepared by reaction of the ligand of formula (I.1) or formula (II) with a cerium salt. Usually, the cerium salt is soluble in the reaction medium. Suitable salts are cerium ammonium nitrate and cerium ammonium sulfate. The ligands are either commercially available or they can be prepared by a synthesis known to the skilled person.

The heteroleptic compounds of formula (I) are prepared by

- mixing two different homoleptic cerium compounds in a suitable solvent,
- mixing a homoleptic cerium compound with a ligand or its alkali/alkaline earth salt which is different from the ligands of the cerium compound used,
- vapor deposition of two different homoleptic cerium compounds,
- vapor deposition (vapor co-condensation) of homoleptic cerium compounds with a ligand different from the ligands of the cerium compound used.

In the cerium compound of formula (I), $L_1$ and $L_2$ are tetradentate ligands independently selected from ligands of formula (I.1) or formula (II)

(I.1)

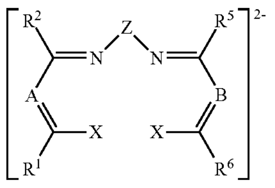

(II)

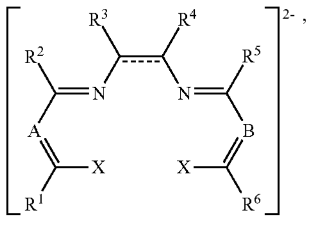

wherein the radicals X, Z, A, B, $R^1$, $R^2$, $R^3$, $R^4$, $R^5$ and $R^6$ have the meanings defined above and below.

In a preferred embodiment, Z is $C_2$-$C_3$ alkylene, $C_2$-$C_3$ alkenylene, wherein alkylene or alkenylene are unsubstituted or substituted with 1, 2, 3, 4, 5, or 6 identical or different radicals $R^{12}$; or 2 or 3 of the carbon atoms of the bridging group are part of a 1-nuclear or 2-nuclear $C_6$-$C_{10}$ aromatic or heteroaromatic ring system, said heteroaromatic ring system having from 4 to 13 carbon atoms and having 1, 2 or 3 identical or different heteroatoms or heteroatom-containing groups as ring members, selected from N, $NR^8$, O, S, SO and $SO_2$ and wherein the aromatic or heteroaromatic ring system is unsubstituted or substituted with 1, 2, 3, 4 or 5 identical or different radicals $R^9$, wherein $R^{12}$ and $R^9$ are defined above and below.

Preferred are cerium compound of formula (I), wherein the ligands $L_1$ and $L_2$ are independently selected ligands of formula (II).

Preferred are ligands of formula (I.1) or (II), wherein $R^1$, $R^2$, $R^5$ and $R^6$ are independently selected from hydrogen, CN, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR_{4a}R_{4b}$ and group A consisting of A1, A2, A3, A4, A5, A6, A7, A8, A9, A10, A11, A12, A13, A14, A15, A16, A17, A18 and A19

A 1

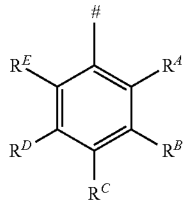

A 2

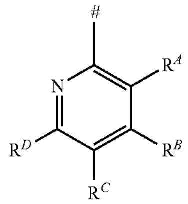

A 3

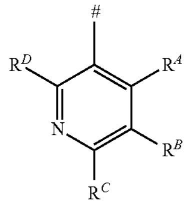

A 4

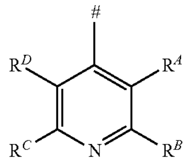

-continued

A 5

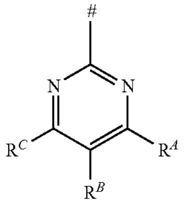

A 6

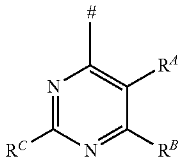

A 7

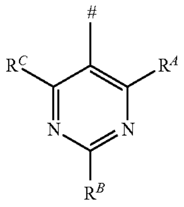

A 8

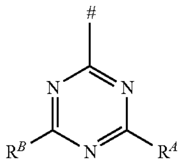

A 9

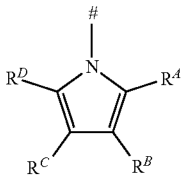

A 10

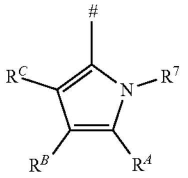

A 11

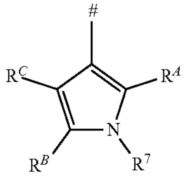

A 12

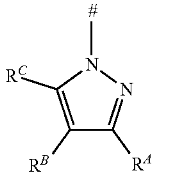

-continued

A 13

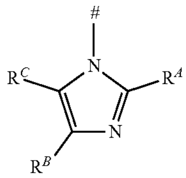

A 14

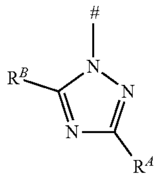

A 15

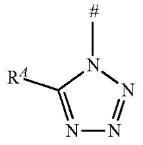

A 16

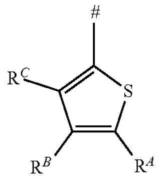

A 17

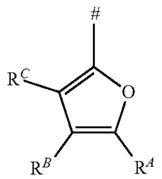

A 18

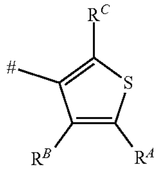

A 19

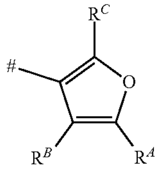

wherein # denotes the bond to the group of formula (I.1) or (II) wherein $R^A$, $R^B$, $R^C$, $R^D$ and $R^E$ are independently selected from hydrogen, CN, halogen, $C_1$-$C_4$ alkyl and $C_1$-$C_4$ haloalkyl; or $R^1$ and A together with the carbon atom to which they are attached form a $C_6$-$C_{14}$ aryl group, wherein aryl is unsubstituted or substituted with 1, 2, 3 or 4 identical or different radicals $R^9$; or $R^6$ and B together with the carbon atom to which they are attached form a $C_6$-$C_{14}$ aryl group, wherein aryl is unsubstituted or substituted with 1, 2, 3 or 4 identical or different radicals $R^9$;

$R^{4a}$, $R^{4b}$ are independently selected from hydrogen, $C_1$-$C_6$ alkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl; and $R^{10}$ is selected from CN, halogen, $C_1$-$C_4$ alkyl and $C_1$-$C_4$ haloalkyl.

Irrespective of their occurrence, the radicals $R^A$, $R^B$, $R^C$, $R^D$ and $R^E$ are preferably selected from hydrogen, CN, fluorine, chlorine, $C_1$-$C_4$ alkyl, $C_1$-$C_4$ fluoroalkyl and $C_1$-$C_4$ chloroalkyl.

Particularly preferred are the radicals $R^A$, $R^B$, $R^C$, $R^D$ and $R^E$ independently of one another selected from hydrogen, CN, $C_1$-$C_4$ fluoroalkyl, fluorine and chlorine. In particular, the radicals $R^A$, $R^B$, $R^C$, $R^D$ and $R^E$ independently of one another represent hydrogen or $CF_3$.

In one embodiment, $R^1$, $R^2$, $R^5$ and $R^6$, in formula (I.1) or (II), are independently selected from hydrogen, $C_1$-$C_4$ alkyl, $C_1$-$C_4$ haloalkyl, and A1

A1

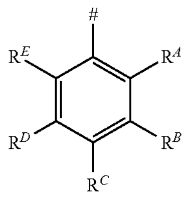

# denotes the bond to the remaining molecule of formula (II), and wherein $R^A$, $R^B$, $R^C$, $R^D$ and $R^E$ are independently selected from hydrogen, CN, fluorine, chlorine, $C_1$-$C_4$ alkyl, $C_1$-$C_4$ fluoroalkyl and $C_1$-$C_4$ chloroalkyl, preferably selected from hydrogen, CN, fluorine and chlorine; or $R^1$ and A together with the carbon atom to which they are attached form a phenyl ring, wherein phenyl is unsubstituted or substituted with 1, 2, 3 or 4 identical or different radicals $R^9$; or $R^6$ and B together with the carbon atom to which they are attached form a phenyl ring, wherein phenyl is unsubstituted or substituted with 1, 2, 3 or 4 identical or different radicals $R^9$;

$R^9$ is selected from CN, halogen, $C_1$-$C_4$ alkyl, $C_1$-$C_4$ haloalkyl and phenyl, wherein phenyl is unsubstituted or substituted with 1, 2, 3, 4 or 5 identical or different substituents selected from $C_1$-$C_4$ alkyl or $C_1$-$C_4$ haloalkyl.

In another embodiment, in formula (I.1) or (II), $R^1$ and $R^6$ are independently selected from $CF_3$ and A1, wherein $R^A$, $R^B$, $R^C$, $R^D$ and $R^E$ are independently selected from CN, $CF_3$, fluoro and chloro;

$R^2$ and $R^5$ are independently selected from hydrogen, $CF_3$ and A1, wherein $R^A$, $R^B$, $R^C$, $R^D$ and $R^E$ are independently selected from hydrogen, CN, $CF_3$, fluorine and chlorine; or $R^1$ and A together with the carbon atom to which they are attached form a phenyl ring, wherein phenyl is unsubstituted or substituted with 1 or 2 identical or different radicals $R^9$; or $R^6$ and B together with the carbon atom to which they are attached form a phenyl ring, wherein phenyl is unsubstituted or substituted with 1 or 2 identical or different radicals $R^9$;

$R^9$ is selected from CN, halogen, $C_1$-$C_2$ alkyl, $C_1$-$C_2$ haloalkyl.

In a particular embodiment, in formula (I.1) or (II), $R^1$ and $R^6$ are independently selected from hydrogen, $CF_3$, and A1, wherein $R^A$, $R^B$, $R^C$, $R^D$ and $R^E$ are independently selected from hydrogen and $CF_3$;

$R^2$ and $R^5$ are independently selected from hydrogen, $CF_3$, and A1, wherein $R^A$, $R^B$, $R^C$, $R^D$ and $R^E$ are independently selected from hydrogen and $CF_3$;

$R^1$ and A together with the carbon atom to which they are attached form a phenyl ring, wherein phenyl is unsubstituted or substituted with 1 or 2 identical or different radicals $R^9$;

$R^6$ and B together with the carbon atom to which they are attached form a phenyl ring, wherein phenyl is unsubstituted or substituted with 1 or 2 identical or different radicals $R^9$;

$R^9$ is selected from CN, F, Cl and $CF_3$.

In another particular embodiment, $R^2$ and $R^5$ in formula (I.1) or (II), are independently selected from hydrogen and $CF_3$ and $R^1$ and $R^6$ are independently selected from $CF_3$ and A1, wherein $R^A$, $R^B$, $R^C$, $R^D$ and $R^E$ are hydrogen or $CF_3$, or $R^1$ and A together with the carbon atom to which they are attached form a phenyl ring, wherein phenyl is unsubstituted or substituted with 1 or 2 identical or different radicals $R^9$; or $R^6$ and B together with the carbon atom to which they are attached form a phenyl ring, wherein phenyl is unsubstituted or substituted with 1 or 2 identical or different radicals $R^9$;

$R^9$ is selected from for CN, F, Cl and $CF_3$.

Preferred are ligands of formula (II), wherein in formula (II) $R^3$ and $R^4$ are independently selected from hydrogen, CN, $C_1$-$C_6$ alkyl, $C_1$-$C_6$ haloalkyl, $C_1$-$C_6$ alkoxy and $C_1$-$C_6$ haloalkoxy, or $R^3$ and $R^4$ together with the carbon atoms to which they are attached form a $C_6$-$C_{14}$ aryl group wherein aryl is unsubstituted or substituted with 1, 2, 3 or 4 identical or different radicals $R^9$;

$R^9$ is selected from CN, halogen, $C_1$-$C_6$ alkyl, $C_1$-$C_6$ haloalkyl or $C_6$-$C_{14}$ aryl, wherein aryl is unsubstituted or substituted with 1, 2, 3, 4 or 5 identical or different substituents selected from $C_1$-$C_4$ alkyl or $C_1$-$C_4$ haloalkyl.

Particularly preferred are ligands of the formula (II) in which formula (II) $R^3$ and $R^4$ are selected independently of one another from hydrogen, CN, $C_1$-$C_4$-alkyl, $C_1$-$C_4$-haloalkyl and phenyl, wherein phenyl is unsubstituted or substituted by 1, 2, 3 or 4 identical or different radicals $R^9$, or $R^3$ and $R^4$ together with the carbon atoms to which they are attached form a phenyl ring, wherein phenyl is unsubstituted or substituted by 1, 2, 3 or 4 identical or different radicals $R^9$;

$R^9$ is selected from CN, halogen, $C_1$-$C_4$-alkyl, $C_1$-$C_4$-haloalkyl or phenyl, where phenyl is unsubstituted or substituted by 1, 2, 3 or 4 identical or different substituents selected from $C_1$-$C_4$-alkyl or $C_1$-$C_4$-haloalkyl.

Particularly preferred are ligands of formula (II), wherein $R^3$ and $R^4$ in formula (II) are independently selected from hydrogen, CN, $C_1$-$C_2$ alkyl and $CF_3$;

$R^3$ and $R^4$ together with the carbon atoms to which they are attached form a phenyl group, wherein phenyl is unsubstituted.

Preferred are ligands of formula (I.1) or (II), wherein in formula (II), wherein A and B are independently a radical $CR^7$ and $R^7$ is selected from hydrogen, CN, nitro, halogen and group B consisting of B1, B2, B3, B4, B5, B6, B7, B8, B9, B10, B11, B12, B13, B14 and B15

B 1

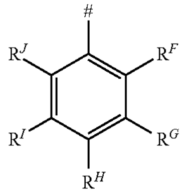

B 2

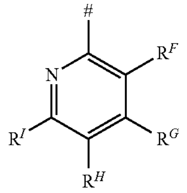

B 3

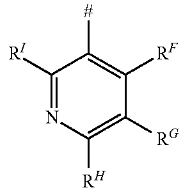

B 4

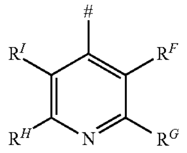

B 5

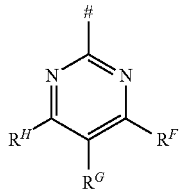

B 6

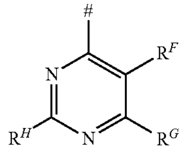

B 7

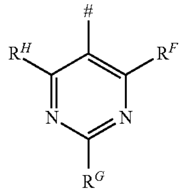

B 8

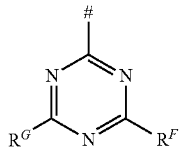

-continued

B 9

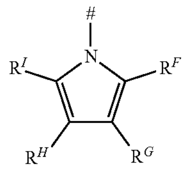

B 10

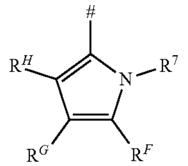

B 11

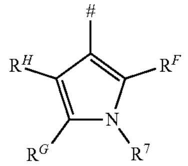

B 12

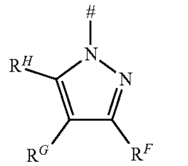

B 13

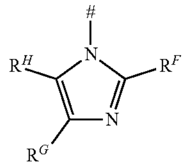

B 14

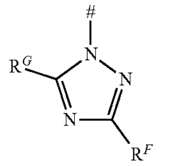

B 15

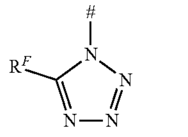

wherein # denotes the bond to the group of formula (II), and wherein $R^F$, $R^G$, $R^H$, $R^I$ and $R^J$ are independently selected from hydrogen, CN, halogen, $C_1$-$C_4$ alkyl and $C_1$-$C_4$ haloalkyl.

Irrespective of their occurrence, the radicals $R^F$, $R^G$, $R^H$, $R^I$ and $R^J$ are preferably selected from hydrogen, CN, fluorine, chlorine, $C_1$-$C_4$-alkyl, $C_1$-$C_4$ fluoroalkyl and $C_1$-$C_4$ chloroalkyl. In a preferred embodiment, the radicals $R^F$, $R^G$, $R^H$, $R^I$ and $R^J$ independently of one another are hydrogen, CN, fluorine or chlorine.

Preferred are ligands of the formula (I.1) or (II), wherein in formula (II), wherein A and B are independently of one another, a radical $CR^7$ and $R^7$ is selected from hydrogen, CN, nitro, halogen, $C_1$-$C_2$ alkyl, $C_1$-$C_2$ haloalkyl and B1, in which $R^F$, $R^G$, $R^H$, $R^I$ and $R^J$ are, independently of one another, selected from hydrogen, CN, fluorine and chlorine.

Particularly preferred are ligands of formula (I.1) or (II), wherein in formula (II), wherein A and B are independently a radical $CR^7$ and $R^7$ is selected from hydrogen, CN, nitro, halogen, $C_1$-$C_2$ alkyl and $C_1$-$C_2$ haloalkyl. In particular, $R^7$ is selected from hydrogen, CN, nitro, fluorine and chlorine, especially hydrogen, fluorine and CN.

In one embodiment A, ligands of formula (II) are selected from formula (I.A)

(I.A)

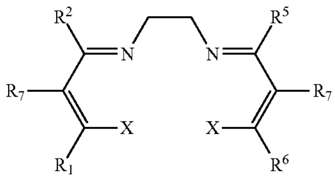
,

X is O, $R^1$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above, $R^2$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above, $R^5$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above, $R^6$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above, $R^7$ is selected from hydrogen, CN, nitro, halogen, $C_1$-$C_2$ alkyl and $C_1$-$C_2$ haloalkyl.

In one embodiment B, ligands of formula (II) are selected from formula (I.B)

(I.B)

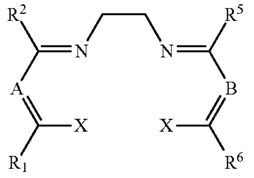

wherein

X represents O;

$R^1$ and A together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl being unsubstituted or substituted by 1, 2, 3 or 4 identical or different radicals $R^9$;

$R^2$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^5$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^6$ and B together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl is unsubstituted or substituted with 1, 2, 3 or 4 identical or different radicals $R^9$.

In one embodiment C, ligands of formula (II) are selected from formula (I.C)

(I.C)

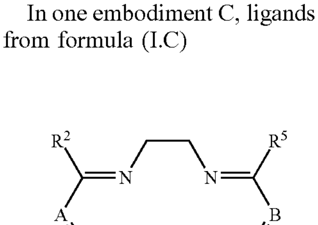

wherein

X represents O;

$R^1$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^2$ and A together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl is unsubstituted or substituted with 1, 2, 3 or 4 identical or different radicals $R^9$;

$R^5$ and B together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl is unsubstituted or substituted with 1, 2, 3 or 4 identical or different radicals $R^9$;

$R^6$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above.

In an embodiment D, ligands of formula (II) are selected from formula (I.D)

(I.D)

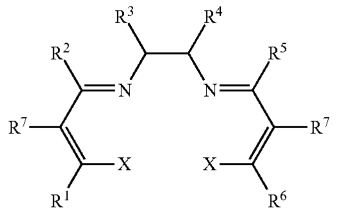

$R^1$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^2$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^3$ and $R^4$ together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl are unsubstituted or substituted with 1, 2, 3 or 4 identical or different radical $R^9$;

$R^5$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^6$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^7$ is selected from hydrogen, CN, nitro, halogen, $C_1$-$C_2$ alkyl and $C_1$-$C_2$ haloalky.

In one embodiment E, ligands of formula (II) are selected from formula (I.E)

(I.E)

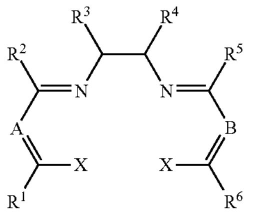

wherein $R^1$ and A together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl is unsubstituted or substituted with 1, 2, 3 or 4 identical or different radicals $R^9$;

$R^2$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^3$ and $R^4$ together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl are unsubstituted or substituted with 1, 2, 3 or 4 identical or different radical $R^9$;

$R^5$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^6$ and B together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl is unsubstituted or substituted with 1, 2, 3 or 4 identical or different radicals $R^9$.

In one embodiment F, ligands of formula (II) are selected from formula (I.F)

(I.F)

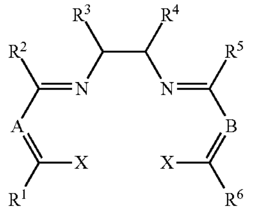

wherein $R^1$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above;

$R^2$ and A together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl is unsubstituted or substituted with 1, 2, 3 or 4 identical or different radicals $R^9$;

$R^3$ and $R^4$ together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl is unsubstituted or substituted with 1, 2, 3 or 4 identical or different radicals $R^9$;

$R^5$ and B together with the carbon atom to which they are attached form a $C_6$-$C_{14}$ aryl group or hetaryl group having 3 to 6 carbon atoms, hetaryl having 1, 2 or 3 heteroatoms or heteroatom-containing groups as ring members selected from N and $NR^8$, wherein aryl and hetaryl is unsubstituted or substituted with 1, 2, 3 or 4 identical or different radicals $R^9$;

$R^6$ is selected from hydrogen, CN, $C_1$-$C_6$ alkyl, $C_1$-$C_6$ haloalkyl, $C_3$-$C_7$ cycloalkyl, wherein $C_3$-$C_7$ cycloalkyl is unsubstituted or substituted with 1, 2, 3, 4, 5 or 6 identical or different substituents selected from CN, halogen, $C_1$-$C_4$ alkyl and $C_1$-$C_4$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19 as defined above.

In a preferred embodiment, the compounds of formula (I), wherein in the ligands of formula (II)

(II)

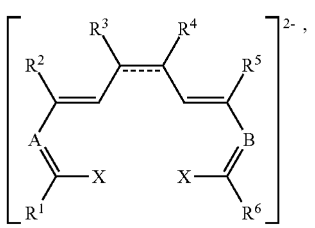

wherein $\overset{-----}{=====}$ between the group $CR^3$-$CR^4$ refers to a single or double bond, X is O;

A and B are independently $CR^7$, where $R^7$ is selected from H and CN;

$R^1$ and $R^6$ are independently selected from hydrogen, $CH_3$, $CF_3$, $C_2F_5$ and phenyl; or $R^1$ and A together with the carbon atom to which they are attached form [4-(trifluoro-methyl)phenyl], or $R^6$ and B together with the carbon atom to which they are attached form [4-(trifluoro-methyl)phenyl];

$R^3$ and $R^4$ represent hydrogen, or $R^3$ and $R^4$ together with the carbons to which they are attached form phenyl or (3,4-difluorophenyl);

$R^2$ and $R^5$ are independently selected from hydrogen, $CH_3$, $CF_3$, $C_2F_5$, phenyl and [3-chloro-4-(trifluoromethyl)phenyl].

In particular, the compounds are selected from

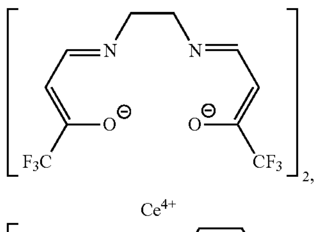

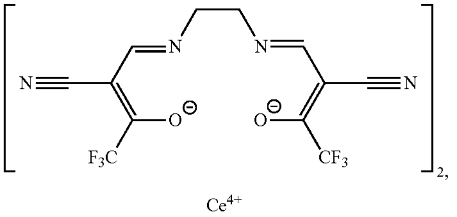

-continued

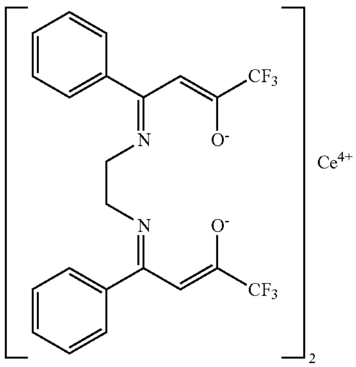

,

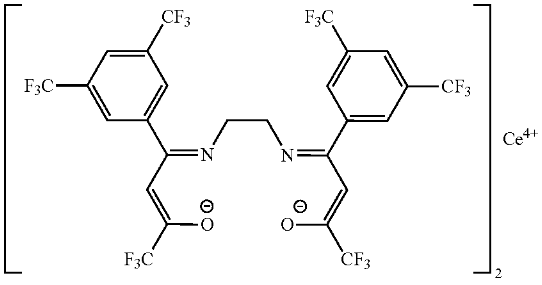

,

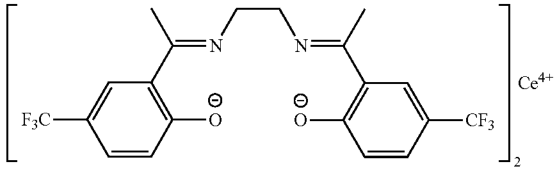

,

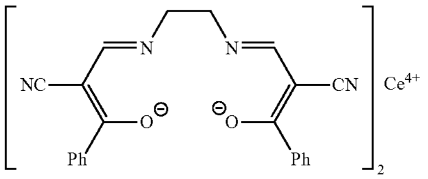

,

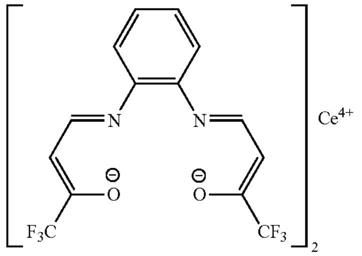

,

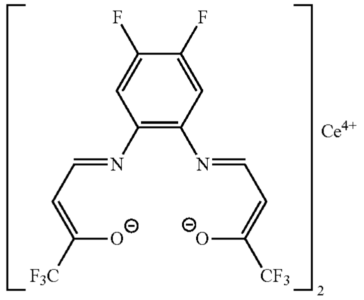

,

-continued

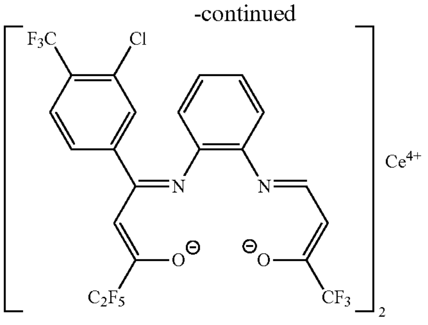

.

Irrespective of their occurrence, the radicals $R^{4a}$ and $R^{4b}$ are preferably selected from hydrogen and $C_1$-$C_4$ alkyl.

Irrespective of their occurrence, the radical $R^8$ is preferably selected from $C_1$-$C_4$ alkyl and $C_1$-$C_4$ haloalkyl.

Irrespective of its occurrence, the radical $R^9$ is preferably selected from CN, halogen, $C_1$-$C_4$ alkyl, $C_1$-$C_4$ haloalkyl and phenyl, wherein phenyl is unsubstituted or substituted by 1, 2, 3, 4 or 5 identical or different radicals selected from $C_1$-$C_4$ alkyl or $C_1$-$C_4$ haloalkyl. In particular, $R^9$ is selected from CN, halogen, $C_1$-$C_2$ alkyl and $C_1$-$C_2$ haloalkyl, In particular, $R^9$ is selected from CN, F, Cl and $CF_3$.

Irrespective of its occurrence, the radical $R^{12}$ is preferably selected from halogen, CN, $C_1$-$C_4$ alkyl, $C_1$-$C_4$ haloalkyl and phenyl, wherein phenyl is unsubstituted or substituted by 1, 2, 3 or 4 identical or different radicals $R^9$.

Component

In the context of the invention, an electronic component is understood to be a discrete or integrated electrical component, which uses the properties of compounds of the general formula (I) or semiconductor matrix materials containing a compound of the general formula (I). In a special embodiment, the electronic component has a layer structure comprising in particular 2, 3, 4, 5, 6, 7 or more layers, wherein at least one of the layers contains at least one compound of the general formula (I). Each of the layers may also contain inorganic materials, or the component may also comprise layers, which are composed entirely from inorganic materials.

Preferably, the electronic component is selected from organic field effect transistors (OFETs), organic electroluminescent devices, organic solar cells (OSCs), devices for electrophotography, organic optical detectors, organic photodetector organic photoreceptors, light-emitting electrochemical cells (LECs) and organic laser diodes. Organic field effect transistors (OFETs) are preferably organic thin film transistors (OTFTs). Organic electroluminescent devices are preferably organic light-emitting diodes (OLEDs). Organic solar cells are preferably exciton solar cells, dye sensitized solar cells (DSSCs) or perovskite solar cells. Devices for electrophotography are preferably photoconductive materials in organic photoconductors (OPC).

Preferably, the electronic component according to the invention is in the form of an organic light-emitting diode, an organic solar cell, a photovoltaic cell, an organic sensor, an organic diode or an organic transistor, preferably a field-effect transistor or thin-film transistor or perovskite solar cell.

The electronic component may be preferably an organic electroluminescent device, in particular in the form of an organic light-emitting diode (OLED). An organic electroluminescent device comprises a cathode, an anode and at least one emitting layer. In addition to these layers, it may also comprise other layers, e.g. one or more hole injection layers, hole transport layers, hole blocking layers, electron transport layers, electron injection layers, exciton blocking layers, electron blocking layers and/or charge generation layers. Intermediate layers, which have e.g. an exciton-blocking-function can also be inserted between two emitting layers. Not all of these layers must necessarily be present.

A preferred embodiment is an electronic component, in particular in the form of an OLED, wherein the layer comprising the compound of formula (I) is a hole transport layer or a hole injection layer. Generally, a hole injection layer is a layer which facilitates electron injection from the anode into the organic semiconductor matrix material. The hole injection layer can be placed directly adjacent to the anode. A hole transport layer transports the holes from the anode to the emitting layer and is located between a hole injection layer and an emitting layer.

A preferred embodiment is an electronic component in the form of an organic solar cell. Generally organic solar cells are layered and usually comprises at least the following layers: anode, at least one photoactive layer and cathode. These layers are generally applied to a substrate commonly used for this purpose. The photoactive region of the solar cell may comprise two layers, each of which has a homogeneous composition and forms a flat donor-acceptor heterojunction. A photoactive region can also comprise a mixed layer and form a donor-acceptor heterojunction in the form of a donor-acceptor bulk heterojunction. In addition to these layers, the organic solar cell can also comprises other layers, e.g. selected from

- Layers with electron transport layer properties (electron transport layer, ETL),
- Layers comprising a hole-conducting material (hole transport layer, HTL), these must not to absorb radiation,
- Exciton and hole blocking layers (e.g. EBLs), these must not absorb, and
- Multiplier layers.

Another preferred embodiment is an electronic component in the form of an organic solar cell, wherein the layer, which comprises the compound of formula (I), has electron conductivity properties (electron transport layer, ETL).

A special embodiment is an electronic component, especially in the form of an organic solar cell, wherein the layer, which comprises at least one of the compounds of formula (I) is part of a pn-junction connecting a light absorbing unit to an additional light absorbing unit in a tandem device or in a multistacked device and/or a pn-junction connecting a cathode or an anode to a light absorbing unit.

Another preferred embodiment is an electronic component comprising an electron transport layer comprising at least one compound of formula (I).

Semiconductor Matrix Materials

The compounds of formula (I) according to the invention and used according to the invention, as well as their charge transfer complexes, their reduction products, can be used as doping agents in organic semiconductor matrix materials, in particular as p-dopant in hole transport layers. The doped semiconductor matrix material, preferably comprising at least one electron donor and at least one compound of the formula (I), as defined above.

Suitable diaminoterphenyls are described in DE 102012007795.

Diaminotrimethylphenylindanes are described in WO 2018/206769.

In particular, the electron donors are selected from 4,4',4"-tris(N-(2-naphthyl)-N-phenyl-amino)triphenylamine (2-TNATA), 4,4',4"-tris(N-3-methylphenyl-N-phenyl-amino)triphenylamine (m-MTDATA), N,N,N',N'-tetrakis(4-methoxy-phenyl)benzidine (MeO-TPD), (2,2',7,7'-tetrakis-(N,N-diphenylamino)-9,9'-spirobifluorene (spiro-TTB), N,N'-bis(naphthalene-1-yl)-N,N'-bis(phenyl)-benzidine, N,N'-bis(naphthalene-1-yl)-N,N'-bis(phenyl)-9,9-spiro-bifluorene, 9,9-bis[4-(N,N-bis-biphenyl-4-yl-amino)phenyl]-9H-fluorene, 2,2'-bis[N,N-bis(biphenyl-4-yl)amino]-9,9-spiro-bifluorene, N,N'-((9H-fluorene-9,9-diyl)bis(4,1-phenylene))bis(N-([1,1'-biphenyl]-4-yl)-[1,1'-biphenyl]-4-amine) (BPAPF), N,N'-bis(phenanthrene-9-yl)-N,N'-bis(phenyl)-benzidine, 1,3,5-tris{4-[bis(9,9-dimethyl-fluorene-2-yl)amino]phenyl}benzene, tri(terphenyl-4-yl)amine, N-(4-(6-((9,9-dimethyl-9H-fluorene-2-yl)(6-methoxy-[1,1'-biphenyl]-3-yl)amino)-1,3,3-trimethyl-2,3-dihydro-1H-indene-1-yl)phenyl)-N-(6-methoxy-[1,1'-biphenyl]-3-yl)-9,9-dimethyl-9H-fluorene-2-amine, N-([1,1'-biphenyl]-4-yl)-N-(4-(6-([1,1'-biphenyl]-4-yl(9,9-dimethyl-9H-fluorene-2-yl)amino)-1,3,3-trimethyl-2,3-dihydro-1H-indene-1-yl)phenyl)-9,9-dimethyl-9H-fluorene-2-amine, N,N-di([1,1'-biphenyl]-4-yl)-3-(4-(di([1,1'-biphenyl]-4-yl)amino)phenyl)-1,1,3-trimethyl-2,3-dihydro-1H-indene-5-amine, N-(4-(6-(bis(9,9-dimethyl-9H-fluorene-2-yl)amino)-1,3,3-trimethyl-2,3-dihydro-1H-inden-1-yl)phenyl)-N-(9,9-dimethyl-9H-fluorene-2-yl)-9,9-dimethyl-9H-fluorene-2-amine, N-(4-(6-(9,9'-spirobi[fluorene]-2-yl(9,9-dimethyl-9H-fluorene-2-yl)amino)-1,3,3-trimethyl-2,3-dihydro-1H-inden-1-yl)phenyl)-N-(9,9-dimethyl-9H-fluoren-2-yl)-9,9'-spirobi[fluorene]-2-amine, N-(4-(6-(dibenzo[b,d]furane-2-yl(9,9-dimethyl-9H-fluorene-2-yl)amino)-1,3,3-trimethyl-2,3-dihydro-1H-indene-1-yl)phenyl)-N-(9,9-dimethyl-9H-fluorene-2-yl)dibenzo[b,d]furan-2-amine, 9-(4-(6-(9H-carbazol-9-yl)-1,3,3-trimethyl-2,3-dihydro-1H-inden-1-yl)phenyl)-9H-carbazole, N-([1,1'-biphenyl]-4-yl)-3-(4-([1,1'-biphenyl]-4-yl(4-methoxyphenyl)amino)phenyl)-N-(4-methoxyphenyl)-1,1,3-trimethyl-2,3-dihydro-1H-inden-5-amine, 3-(4-(bis(6-methoxy-[1,1'-biphenyl]-3-yl)amino)phenyl)-N,N-bis(6-methoxy-[1,1'-biphenyl]-3-yl)-1,1,3-trimethyl-2,3-dihydro-1H-indene-5-amine, N1-([1,1'-biphenyl]-4-yl)-N1-(4-(6-([1,1'-biphenyl]-4-yl(4-(diphenylamino)phenyl)amino)-1,3,3-trimethyl-2,3-dihydro-1H-inden-1-yl)phenyl)-N4,N4-diphenylbenzene-1,4-diamine, N,N-di([1,1'-biphenyl]-4-yl)-4'-(6-(4-(di([1,1'-biphenyl]-4-yl)amino)phenyl)-1,3,3-trimethyl-2,3-dihydro-1H-indene-1-yl)-[1,1'-biphenyl]-4-amine, N-(4-(5-(bis(9,9-dimethyl-9H-fluorene-2-yl)amino)-1,3,3-trimethyl-2,3-dihydro-1H-indene-1-yl)phenyl)-N-(9,9-dimethyl-9H-fluorene-2-yl)-9,9-dimethyl-9H-fluorene-2-amine, N-(4-(6-(bis(9,9-dimethyl-9H-fluorene-2-yl)amino)-1,3,3-trimethyl-2,3-dihydro-1H-indene-1-yl)-phenyl)-N-(9,9-dimethyl-9H-fluorene-2-yl)-9,9-dimethyl-9H-fluorene-2-amine, N,N'-bis(9,9-dimethyl-fluorene-2-yl)-N,N'-diphenyl-benzidine (BF-DPB), N,N'-((9H-fluorene-9,9-diyl)bis(4,1-phenylene))bis(N-([1,1'-biphenyl]-4-yl)-[1,1'-biphenyl]-4-amine) (BPAPF), N4,N4,N4',N4'-tetrakis(9,9-dimethyl-9H-fluorene-2-yl)-[1,1'-biphenyl]-4,4'-diamine (TDMFB), N-([1,1'-biphenyl]-2-yl)-N-(9,9-dimethyl-9H-fluorene-2-yl)-9,9'-spirobi[fluorene]-2-amine, (2,7-bis[N,N-bis(4-methoxyphenyl)amino]-9,9-spirobi[9H-fluorene] (spiro-MeO-TPD), a mixture of N-(4-(5-(bis(9,9-dimethyl-9H-fluorene-2-yl)amino)-1,3,3-trimethyl-2,3-dihydro-1H-inden-1-yl)phenyl)-N-(9,9-dimethyl-9H-fluorene-2-yl)-9,9-dimethyl-9H-fluorene-2-amine and N-(4-(6-(bis(9,9-dimethyl-9H-fluorene-2-yl)amino)-1,3,3-trimethyl-2,3-dihydro-1H-inden-1-yl)phenyl)-N-(9,9-dimethyl-9H-fluorene-2-yl)-9,9-dimethyl-9H-fluorene-2-amine, N-([1,1'-biphenyl]-4-yl)-9,9-dimethyl-N-(4-(9-phenyl-9H-carbazol-3-yl)phenyl)-9H-fluorene-2-amine and mixtures thereof.

Of course, other suitable organic semiconductor matrix materials, especially hole-conducting materials with semi-conducting properties, can also be used.

Doping

The doping can take place in particular in such a manner that the molar ratio of matrix molecule to compounds of formula (I) is 10000:1 to 1:1, preferably 1000:1 to 2:1, especially 5:1 to 100:1.

Preparation of the Doped Semiconductor Matrix Material

The doping of the particular matrix material (in the following also indicated as hole-conducting matrix HT) with the compounds of the general formula (I) according to the invention and used according to the invention can be produced by one or a combination of the following processes:

a) Mixed evaporation in the vacuum with a source for HT and a source for at least one compound of the general formula (I).

b) Sequential deposition of HT and at least one compound of the general formula (I), with subsequent inward diffusion of the doping agent by thermal treatment.

c) Doping of an HT layer by a solution of at least one compound of the general formula (I), with subsequent evaporation of the solvent by thermal treatment.

d) Surface doping of an HT layer by a layer of at least one compound of the general formula (I) applied on either or both surfaces of the HT layer.

e) Preparation of a solution of host and at least one compound of the general formula (I) and forming a film from the solution e.g. by coating, casting or printing techniques or other film preparing techniques known to a person skilled in the art.

Another object of the invention is the use of a compound (I) or a mixture thereof as defined above as organic semiconductor, as redox doping agent in organic semiconductor matrix materials, especially as p-dopant in hole transport layers, as electron transport material, as charge injector in a charge injection layer, as cathode material in organic batteries, as electrochromic material.

A further object of the invention is the use of Ce(III) complex anions obtained by reduction of a compound (I) as defined above or of charge transfer complexes of a compound (I) as defined above with electron donors as organic semiconductor or as electrochromic material.

A further object of the invention is a compound of general formula (I)

$$Ce^{4+}[L_1L_2]^{4-} \quad (I),$$

their charge transfer complexes, their reduction products and mixtures thereof, wherein $L_1$ and $L_2$ are each a tetradentate ligand independently selected from ligands of formula (I.1)

(I.1)

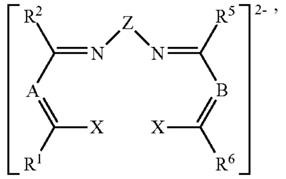

wherein

X independently from each other represents O or S;

Z is a bridging group, which has 2 or 3 carbon atoms between the nitrogen atoms, wherein the carbon atoms each being unsubstituted or substituted by 1, 2, 3, 4, 5 or 6 identical or different radicals $R^{12}$, wherein two adjacent carbon atoms may be linked to one another by a double bond, or 2 or 3 of the carbon atoms are part of a mononuclear, 2-nuclear or 3-nuclear $C_6$-$C_{14}$ aromatic or heteroaromatic ring system, wherein the heteroaromatic ring system has 4 to 13 carbon atoms and has 1, 2 or 3 identical or different heteroatoms or heteroatom-containing groups as ring members selected from N, $NR^8$, O, S, SO and $SO_2$ and wherein the aromatic or heteroaromatic ring system is unsubstituted or substituted by 1, 2, 3, 4 or 5 identical or different radicals $R^9$;

A and B independently from each other represent N or $CR^7$;

$R^1$ and $R^6$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_3$-$C_7$-cycloalkyl, wherein $C_3$-$C_7$-cycloalkyl is unsubstituted or substituted by 1, 2, 3, 4, 5 or 6 identical or different radicals $R^{11}$ $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$; or $R^1$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^6$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^2$ and $R^5$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_3$-$C_7$-cycloalkyl, wherein $C_3$-$C_7$-cycloalkyl is unsubstituted or substituted by 1, 2, 3, 4, 5 or 6 identical or different radicals $R^{11}$, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

$R^2$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^5$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^{4a}R^{4b}$ are independently from each other selected from hydrogen, $C_1$-$C_6$ alkyl and $C_6$-$C_{14}$ aryl, wherein aryl is unsubstituted or substituted with 1, 2, 3, 4 or 5 identical or different radicals $R^{10}$;

$R^7$ is selected from hydrogen, CN, nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl has 1, 2 or 3 identical or different heteroatoms or heteroatom-containing groups as ring members selected from N, $NR^8$, O, S, SO and $SO_2$, wherein aryl and hetaryl are unsubstituted or substituted with 1, 2, 3, 4 or 5 identical or different radicals $R^{10}$;

$R^8$ is selected from hydrogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl;

$R^{10}$ is selected from CN, halogen, $C_1$-$C_4$ alkyl, $C_1$-$C_4$ haloalkyl;

$R^{11}$ is selected from CN, halogen, $C_1$-$C_4$ alkyl, $C_1$-$C_4$ haloalkyl;

$R^{12}$ independently selected from halogen, CN, $C_1$-$C_6$-alkyl, $C_1$-$C_6$-haloalkyl, $C_1$-$C_6$-alkoxy, $C_1$-$C_6$-haloalkoxy, $C_3$-$C_7$-cycloalkyl, where $C_3$-$C_7$-cycloalkyl is unsubstituted or substituted by 1, 2, 3, 4, 5 or 6 identical or different radicals $R^{11}$, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

with the proviso that the following compounds are excluded:

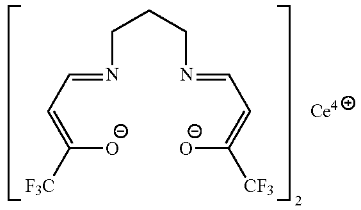

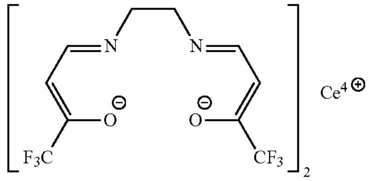

-continued

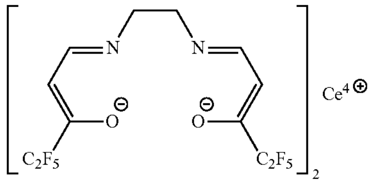

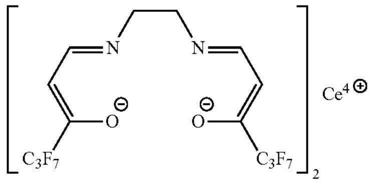

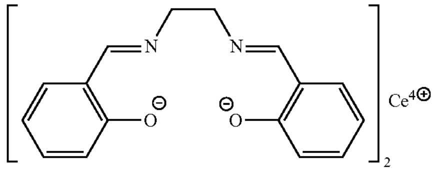

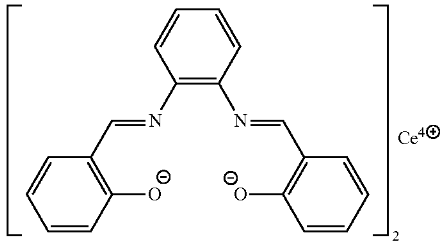

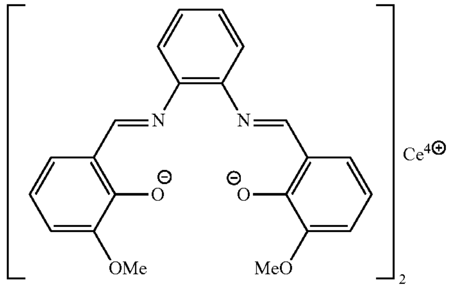

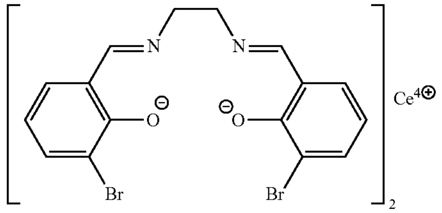

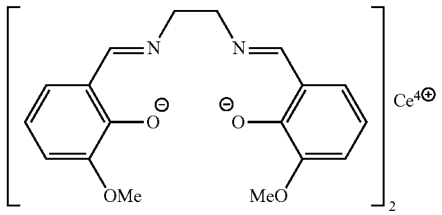

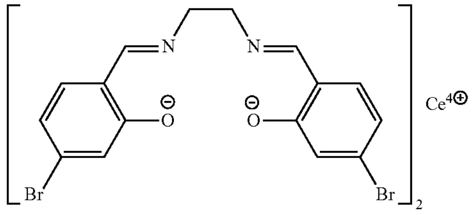

-continued

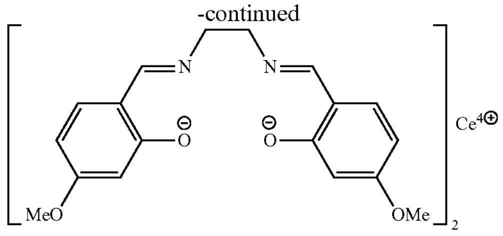

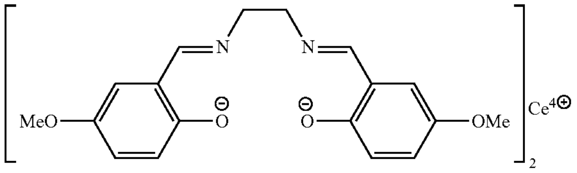

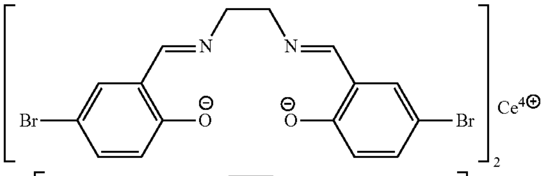

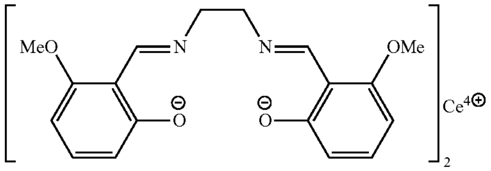

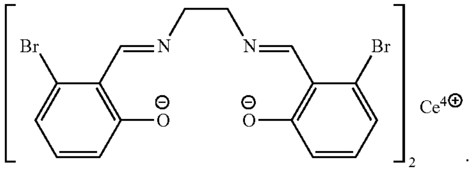

A further object of the invention are compounds of general (I)

$$Ce^{4+}[L_1L_2]^{4-} \quad (I),$$

their charge transfer complexes, their reduction products and mixtures thereof, wherein $L_1$ and $L_2$ are each a tetradentate ligand independently selected from ligands of formula (II)

(II)

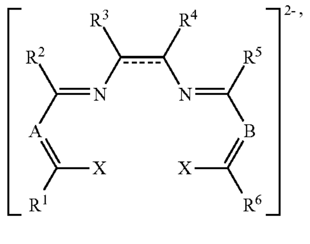

wherein $\overline{=====}$ between the group $CR^3$-$CR^4$ represents a single or double bond;

X independently from each other represents O or S;

A and B independently from each other represent N or $CR^7$; $R^1$ and $R^6$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$; or $R^1$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^6$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^3$ and $R^4$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$, or $R^3$ and $R^4$ together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different $R^9$ radicals;

$R^2$ and $R^5$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

$R^{4a}R^{4b}$ are independently from each other selected from hydrogen, $C_1$-$C_6$ alkyl and $C_6$ $C_{14}$ aryl, wherein aryl is unsubstituted or substituted with 1, 2, 3, 4 or 5 identical or different radicals $R^{10}$;

$R^7$ is selected from hydrogen, CN, nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl has 1, 2 or 3 identical or different heteroatoms or heteroatom-containing groups as ring members selected from N, $NR^8$, O, S, SO and $SO_2$, wherein aryl and hetaryl are unsubstituted or substituted with 1, 2, 3, 4 or 5 identical or different radicals $R^{10}$;

$R^8$ is selected from hydrogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl;

$R^{10}$ is selected from CN, halogen, $C_1$-$C_4$ alkyl, $C_1$-$C_4$ haloalkyl, with the proviso that the following compounds and their reaction products of formula (I) are excluded:

$L_1$=$L_2$=N,N'-bis(4,4,4,-trifluorobut-1-en-3-one)-ethylendiamine, $L_1$=$L_2$=N,N'-bis(4,4,5,5,5-pentafluoropent-1-en-3-one)-ethylendiamine, $L_1$=$L_2$=N,N'-bis(4,4,5,5,6,6,6-heptafluorohex-1-en-3-one)-ethylendiamine and the following compounds and their reaction products:

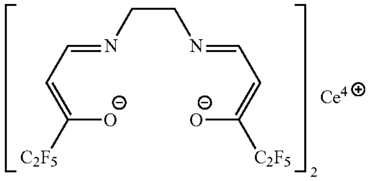

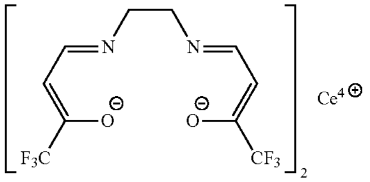

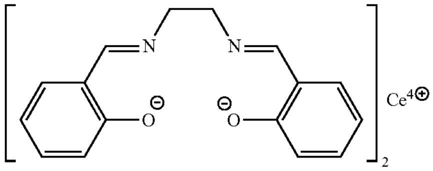

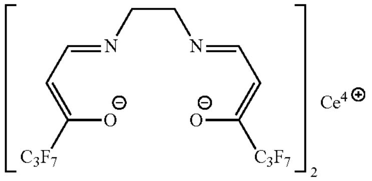

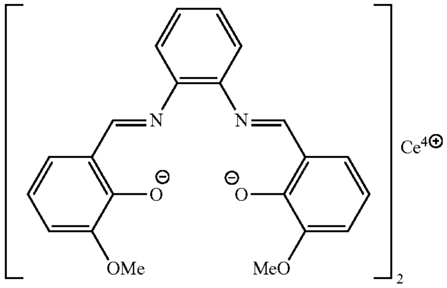

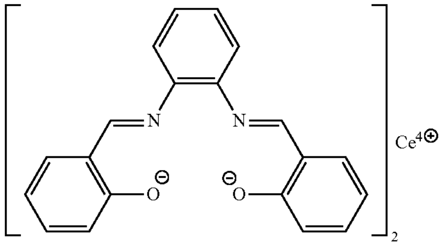

-continued

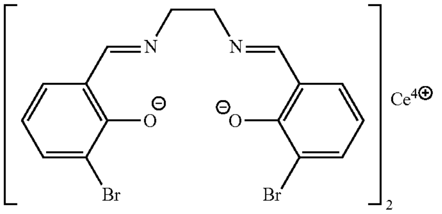

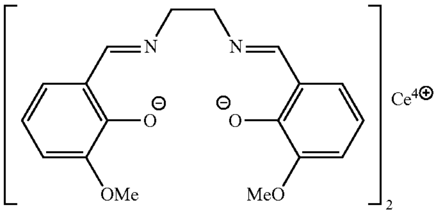

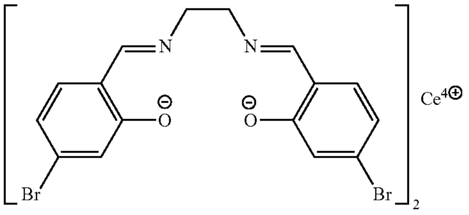

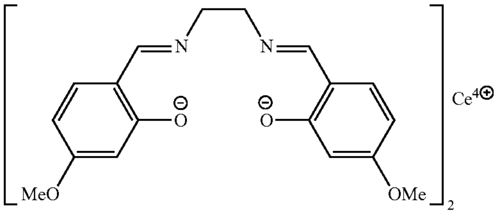

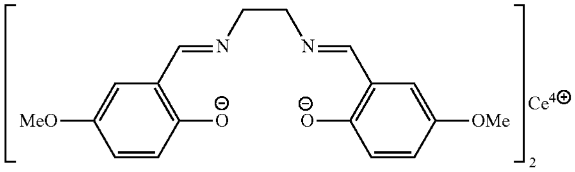

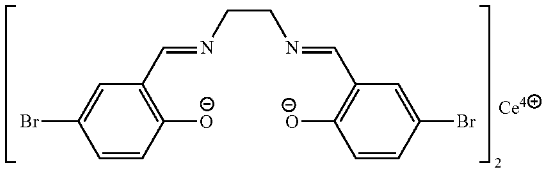

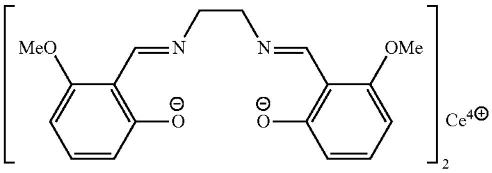

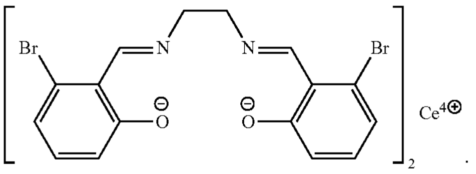

The following examples illustrate the invention without limiting it in any way.

EXAMPLES

Abbreviation

APCI-MS atmospheric pressure chemical ionization-Mass spectrometer

DCM Dichloromethane

DEM Ethylene glycol dimethyl ether

HTM Hole transport material

MeCN Acetonitrile iPrOH Iso-Propanol

EDTA Ethylenediaminetetraacetic acid

Cerium isopropoxide was prepared according to “Gradeff, P. S. et al., *Journal of the less common metals, Vol.* 126, 1986, 335-338.”

Sample Preparation for Conductivity Measurement:

Glass substrates with 50 nm thick patterned Au electrodes with channel length 100 μm were used to prepare the doped thin film samples. The layers were deposited either by thermal evaporation or by deposition from the liquid phase, e.g., with spin coating. Thermal evaporation took place at room temperature in high vacuum (base pressure $<5\times10^{-7}$ mbar). Hole transport material (HTM) and dopant were co-evaporated according to a dopant concentration of 20 wt %, with evaporation rates controlled by two independent quartz crystal microbalances.

The liquid-processed films were spin-coated from a chlorobenzene solution of HTM and dotand at 3000 rpm. The concentration of dotand in the HTM was nominally 10 wt %. The layers were then baked at 80 °C for 5 min. The film thickness was checked by profilometry and ranged from 50 to 110 nm.

Characterization:

The lateral conductivity of the coatings was determined from the slope of the current-voltage characteristics between −10 and 10V. The measurement took place directly after sample preparation for thermal evaporated coatings in-situ in high vacuum, for liquid processed coatings in air.

Synthesis of 1:

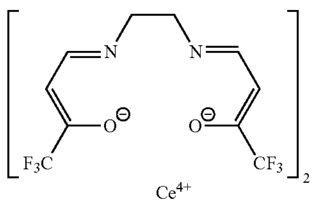

The synthesis was performed according to the literature J. Schläfer, D. Graf, G. Fornalczyk, A. Mettenbörger, S. Mathur, Inorg. Chem. 2016, 55, 5422-5429.

Cyclovoltametry of 1 in dichloromethane (DCM, 200 mV/s, 0.1M $NBu_4PF_6$) resulted in the following: $E_{1/2}$ (vs. $Fc/Fc^+$)=−0.51V.

Compound 1 sublimates without residue at an external temperature of 140 °C and a pressure of 10-2 mbar.

Synthesis of 2:

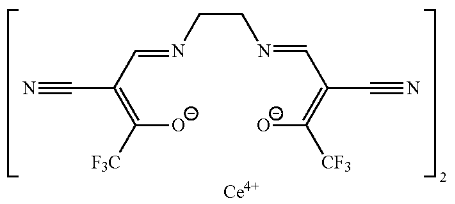

The preparation of 4,4,4-trifluoro-3-oxobutanenitrile was carried out according to WO2005/49033.

4,4,4-Trifluoro-3-oxobutanenitrile (1.9 g, 13.9 mmol) was dissolved in acetic anhydride ($Ac_2O$, 5 ml) and $(EtO)_3CH$ (2.05 g, 13.9 mmol). The reaction mixture was refluxed for one hour. Subsequently, all volatile components were removed in vacuo. The brown residue was dissolved in dichloromethane (DCM 20 ml) and 1,2-diaminoethane (0.2 ml) was added. The white precipitate was filtered off (0.079 g, 0.22 mmol, 1.6%). The mass spectrum of the ligand shows $[M-H]^+$; 353.

To a 0.3M solution of $Ce_2(OiPr)_8(HOiPr)_2$ (0.17 ml, 0.055 mmol) in ethylene glycol dimethyl ether/ipropanol (DME/iOrOH, 1:1 v/v) was added the ligand (76 mg, 0.21 mmol) under $N_2$. After 30 min, the solvent was removed. 0.078 mg of red solid of compound 2 was obtained. The mass spectrum of compound 2 shows $[M-H]^-$; 843.

Cyclic voltametry of 2 in acetonitrile (ACN, 200 mV/s, 0.1M $NBu_4PF_6$) resulted in the following:

$E_{1/2}$(vs. $Fc/Fc^+$)=+0.40V.

Synthesis of 3:

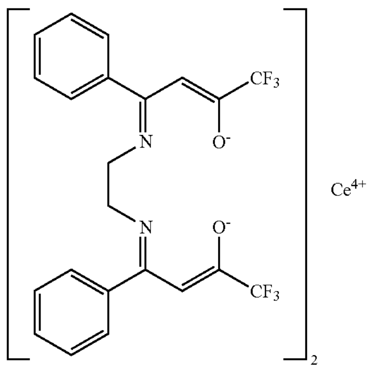

The synthesis of the ligand was performed according to the literature Gurley, L.; Beloukhina, N.; Boudreau, K.; Klegeris, A.; McNeil, W. S. Journal of Inorganic Biochemistry 2011, 105, 6, 858-866.

To a 0.4M solution of $Ce_2(OiPr)_8(HOiPr)_2$ (0.33 ml, 0.131 mmol) in ethylene glycol dimethyl ether/ipropanol (DME/iPrOH) (1:1 v/v) was added 1 (120 mg, 0.26 mmol) under $N_2$. After 30 min, the solvent was removed and the solid was washed with diethyl ether ($Et_2O$). 56 mg of red solid of compound 3 was obtained. The mass spectrum of compound 3 shows $[M-H]^-$; 1047.

Cyclic voltammetry of 3 in acetonitrile (ACN, 200 mV/s, 0.1M $NBu_4PF_6$) resulted in the following: $E_{1/2}$ (vs. $Fc/Fc^+$)=−0.36V.

Synthesis of 4:

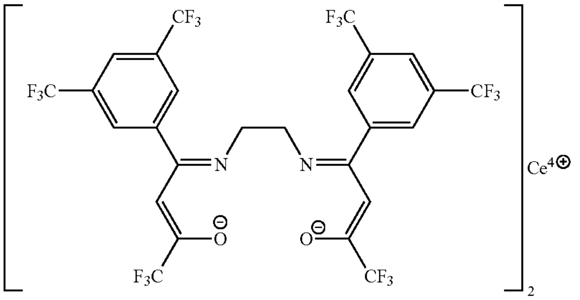

3,5-Bistrifluoromethylacetophenone (8 g, 31.3 mmol) was dissolved in ethanol (40 ml), and acetic acid (0.1 ml) was added. Then 1,2-diaminoethane (0.94 g, 15.6 mmol) was added, and the solution was heated in a pressure tube for 12 h at 90 °C. Upon cooling to −20 °C, colorless crystals were formed, which were filtered off. After drying in vacuo, 2.0 g (0.37 mmol, 24%) of a colorless solid, N1,N2-bis(1-(3,5-bis(trifluoromethyl)phenyl)vinyl)ethane-1,2-diamine, APCI-MS (positive): 537.3 $[M+H]^+$, was obtained.

N1,N2-Bis(1-(3,5-bis(trifluoromethyl)phenyl)vinyl)ethane-1,2-diamine (9.72 g, 18.1 mmol) was suspended in DCM (50 ml) and trifluoroacetic anhydride (8.37 g, 39.8 mmol) were added. After stirring at room temperature for 12 h, the reaction solution was cooled to −20 °C and the white solid was filtered off. The solid was recrystallized from acetonitrile (50 ml) and filtered off. White solid, 4.16 g (5.71 mmol, 31%): 4,4'-(ethane-1,2-diylbis(azanediyl))bis(4-(3,5-bis(trifluoromethyl)phenyl)-1,1,1-trifluorobut-3-en-2-one), APCI-MS (positive): 729.4 $[M+H]^+$.

4,4'-(ethane-1,2-diylbis(azanediyl))bis(4-(3,5-bis(trifluoromethyl)phenyl)-1,1,1-trifluorobut-3-en-2-one) (2 g, 2.74 mmol) were added to a solution of cerium(IV) isopropoxide (0.32M in DME/iPrOH, 4.3 ml, 1.37 mmol). After stirring for 12 h, the suspension was filtered and washed with DME. Red solid, 1.9 g (1.19 mmol, 87%),cerium bis((2Z,2'Z,4Z,4'Z)-4,4'-(ethane-1,2-diylbis(azanylylide))bis(4-(3,5-bis(trifluoromethyl)phenyl)-1,1,1-trifluorobut-2-ene-2-olate)) (4), APCI-MS (positive): 1593 $[M+H]^+$.

The metal complex (4) (538 mg) was sublimed at 200 °C at $4 \cdot 10^{-6}$ mbar. The yield was 335 mg (62%). The metal complex (4) decomposes at 260 °C.

Cyclic voltammetry of 4 in acetonitrile (ACN, 200 mV/s, 0.1M $NBu_4PF_6$) resulted in the following:

$E_{1/2}$(vs. $Fc/Fc^+$)=−0.12V.

When spiro-MeO-TAD (CAS No.: 207739-72-8) was doped with 20 wt % of the dopant (4), an increase in conductivity up to $1.5 \cdot 10^{-6}$ S/cm was measured after solvent processing (spin coating). The intrinsic conductivity of the spiro-MeO-TAD without doping was measured to be $2 \cdot 10^{-8}$ S/cm.

Synthesis of 5:

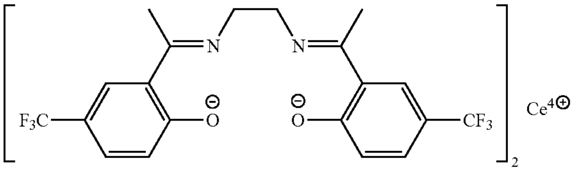

1-(2-hydroxy-5-(trifluoromethyl)phenyl)ethan-1-one (1.19 g, 0.583 mmol) and 1,2-diaminoethane (0.18 g, 0.29 mmol) were dissolved in DCM and stirred for 12 h. The solid was then filtered off. A white solid, 0.63 g (1.45 mmol, 50%), 2,2'+(ethane-1,2-diylbis(azaneylylidene))bis(ethan-1-yl-1-ylidene))bis(4-(trifluoromethyl)phenol) was obtained, APCI-MS (positive): 433.3 $[M+H]^+$.

2,2'-(-(ethane-1,2-diylbis(azaneylylidene))bis(ethan-1-yl-1-ylidene))bis(4-(trifluoromethyl)phenol) (0.59 g, 1.36 mmol) were added to a solution of cerium(IV) isopropoxide (0.32M in DME/iPrOH, 0.68 mmol, 2.12 ml). The solvent was removed and the residue was washed with hexane. The residue was dissolved in $CHCl_3$, filtered, and precipitated with hexane and filtered off. An orange-red solid, 0.42 g (0.42 mmol, 62%), cerium bis((2,2'-((1E,1'E)-(ethane-1,2-diylbis(azanylylidene))bis(ethan-1-yl-1-ylidene))bis(4-(trifluoromethyl)phenolate)) (5) was obtained. APCI-MS (positive): 1001 $[M+H]^+$.

The metal complex (5) (350 mg) was sublimed at 180-200 °C at $4 \cdot 10^{-6}$ mbar. The yield was 12 mg (0.3%).

Cyclic voltammetry of 5 in acetonitrile (ACN, 200 mV/s, 0.1M $NBu_4PF_6$) resulted in the following: $E_{1/2}$ (vs. Fc/$Fc^+$)=+0.3V.

Synthesis of 6:

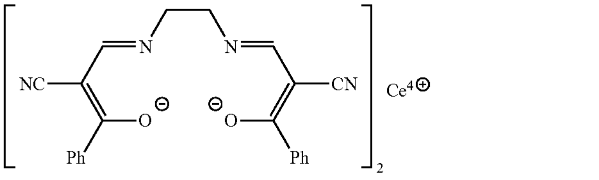

Ethylenediamine (830 mg, 13.6 mmol) was added to a solution of 2-benzoyl-3-ethoxyacrylonitrile (5.54 g, 27.6 mmol) in 50 ml dichloromethane and allowed to stir at room temperature. After 2 h, a precipitate had formed, which was filtered off and washed with dichloromethane. After drying in vacuo, 2.75 g (7.43 mmol, 55%) of (2Z,2'E)-2,2'-((ethane-1,2-diylbis(azanediyl))bis(methanylylidene))bis(3-oxo-3-phenylpropanenitrile) was obtained.

To a solution of cerium isopropoxide (11.25 ml, 3.6 mmol) was added 2.67 g (7.2 mmol) (2Z,2'E)-2,2'-((ethane-1,2-diylbis(azanediyl))bis(methanylylidene))bis(3-oxo-3-phenylpropanenitrile). The brown solid was filtered off and washed with DME (15 ml) and hexane (20 ml). The solid was then washed three times with a total of 200 ml of dichloromethane and the wash solution was filtered. The wash solution was concentrated to half and hexane (100 ml) was added. The microcrystalline dark solid formed was filtered and dried in vacuo. 1.80 g (2.05 mmol, 57%) was obtained of (6). (6) decomposed at 170 °C.

Cyclic voltammetry of 6 in acetonitrile (ACN, 200 mV/s, 0.1M $NBu_4PF_6$) resulted in the following: $E_{1/2}$ (vs. Fc/$Fc^+$)=−0.1V.

Synthesis of 7:

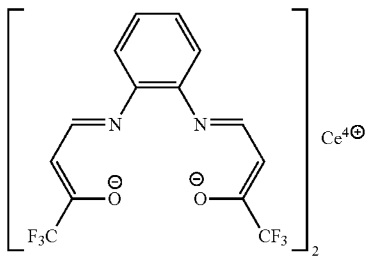

Phenylenediamine (1.62 g, 15 mmol) and (E)-4-ethoxy-1,1,1-trifluorobut-3-en-2-one (5 g, 30 mmol) were added together and stirred for 2 d at room temperature in 100 ml dichloromethane. The solution was concentrated by half then 100 ml of pentane was added. The microcrystalline solid, 4,4'-(1,2-phenylenebis(azanylylidene))bis(1,1,1-trifluorobut-2-en-2-ol) (2.04 g, 5.80 mmol), was filtered and dried in vacuo. 4.12 g (11.7 mmol, 78%) was isolated.

4,4'-(1,2-Phenylenebis(azanylylidene))bis(1,1,1-trifluorobut-2-en-2-ol) (2.04 g, 5.80 mmol) was added to a solution cerium(IV) isopropoxide (0.32M in DME/iPrOH, 9 ml, 2.89 mmol) against. The directly resulting red solid was filtered off and washed with DME. Dark red solid (7) was obtained, 1.08 g (1.39 mmol, 48%). APCI-MS (positive): 841.1 $[M+H]^+$.

The metal complex (7) (1.00 g) was sublimed at 180-210 °C at $3 \cdot 10^{-6}$ mbar. The yield was 205 mg (20%). The metal complex (7) decomposes at 237 °C.

Cyclic voltammetry of 7 in acetonitrile (ACN, 200 mV/s, 0.1M $NBu_4PF_6$) resulted in the following: $E_{1/2}$ (vs. Fc/$Fc^+$)=−0.09V.

Synthesis of 8:

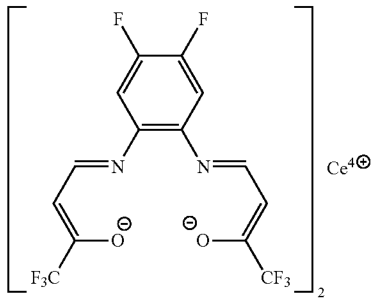

4,5-difluorobenzene-1,2-diamine (2.14 g, 15 mmol) and (E)-4-ethoxy-1,1,1-trifluorobut-3-en-2-one (5 g, 30 mmol) were combined and stirred for 2 d at room temperature in 500 ml of dichloromethane. 100 ml of the dichloromethane was removed in vacuo and 200 ml of pentane was added. The microcrystalline solid, (2Z,2'Z,4E,4'E)-4,4'-((4,5-difluoro-1,2-phenylene)bis(azanylylidene))bis(1,1,1-trifluorobut-2-en-2-ol), was filtered and dried in vacuo. 3.60 g (9.27 mmol, 62%) was isolated.

4,4'-((4,5-Difluoro-1,2-phenylene)bis(azanylylidene))bis(1,1,1-trifluorobut-2-en-2-ol) (2.50 g, 6.44 mmol) was added to a solution of cerium(IV) isopropoxide (0.32M in DME/iPrOH, 4.3 ml, 1.37 mmol). The suspension was filtered and the red solid was washed with a little DME and hexane. A dark red solid, (8), 0.70 g (0.77 mmol, 12%), cerium bis((2Z,2'Z,4E,4'E)-4,4'-((4,5-difluoro-1,2-phenylene)bis(azanylylidene))bis(1,1,1-trifluorobut-2-en-2-olate)) was obtained, APCI-MS (positive): 913 $[M+H]^+$.

The metal complex (8) (700 mg) was sublimed at 180 °C at 3.10-6 mbar. The yield was 150 mg (22%). The metal complex (8) decomposes at 244 °C.

Cyclic voltammetry of 8 in acetonitrile (ACN, 200 mV/s, 0.1M $NBu_4PF_6$) resulted in the following: $E_{1/2}$ (vs. Fc/$Fc^+$)=+0.08V.

When ZnPc (zinc phthalocyanine) was doped with 20 wt % of the dopant (8), an increase in conductivity up to $7.6 \cdot 10^{-5}$ S/cm was measured after co-evaporation in vacuum. The intrinsic conductivity of ZnPc without doping is $<1 \cdot 10^{-8}$ S/cm. (Tietze, M. L., Pahner, P., Schmidt, K., Leo, K., & Lüssem, B. (2015). Advanced Functional Materials, 25(18), 2701-2707).

When MeO-TPD (CAS No.: 122738-21-0) was doped with 20 wt % of the dopant (8), an increase in conductivity up to 1.10-5 S/cm was measured after co-evaporation in vacuum. The intrinsic conductivity of ZnPc without doping is $7 \cdot 10^{-8}$ S/cm. (Sakai, N., Warren, R., Zhang, F., Nayak, S., Liu, J., Kesava, S. V., Lin, Y.-H., Biswal, H. S., Lin, X., Grovenor, C., Malinauskas, T., Basu, A., Anthopoulos, T. D., Getautis, V., Kahn, A., Riede, M., Nayak, P. K., & Snaith, H. J. (2021). Adduct-based p-doping of organic semiconductors. *Nature Materials* 2021 20:9, 20(9), 1248-1254.)

When spiro-MeO-TAD (CAS No.: 207739-72-8) was doped with 20 wt % of dopant (8), an increase in conductivity up to 2.8.10-6 S/cm was measured after solvent processing (spin coating). The intrinsic conductivity of the spiro-MeO-TAD without doping was measured to be $2 \cdot 10^{-8}$ S/cm.

Synthesis of 9:

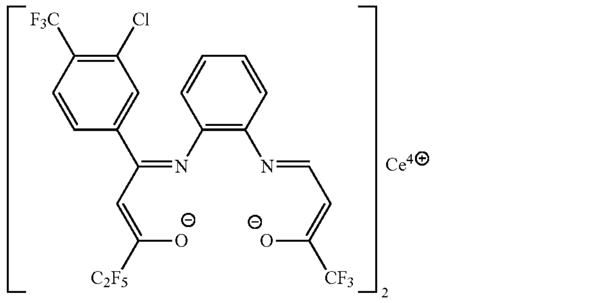

1-(3-Chloro-4-(trifluoromethyl)phenyl)-4,4,5,5-pentafluoropentane-1,3-dione (3.00 g, 8.13 mmol) was suspended in $B(nBuO)_3$ (9.35 g, 40.7 mmol) and 1,2-diaminophenylene (0.88 g, 8.13 mmol) was added. After 15 minutes, the white solid was filtered off and washed with little hexane. A white solid, 2.2 g (4.79 mmol, 59%), 1-((2-aminophenyl)amino)-1-(3-chloro-4-(trifluoromethyl)phenyl)-4,4,5,5-pentafluoropent-1-en-3-one, was obtained. APCI-MS (positive): 459 $[M+H]^+$.

4-Ethoxy-1,1,1-trifluorobut-3-en-2-one (0.73 g, 4.37 mmol) was dissolved in DCM and 1-((2-aminophenyl)amino)-1-(3-chloro-4-(trifluoromethyl)phenyl)-4,4,5,5-pentafluoropent-1-en-3-one (2.0 g, 4.37 mmol) was added. The reaction mixture was stirred for 12 h and then the solvent was removed. The residue was dissolved in acetonitrile and subsequently copper(II) acetate (1.5 g) was added. Water was added to this dark green solution and the solid was filtered off. The solid was purified by column chromatography (chloroform as eluent). The residue was treated with oxalic acid and EDTA, then conc. HCl and chloroform, and the phases were separated. The organic phase was washed with saturated $NaHCO_3$ and saturated NaCl solution and dried ($Na_2SO_4$). The solvent was removed. A white solid, 2.0 g (3.44 mmol, 79%), 1-(3-chloro-4-(trifluoromethyl)phenyl)-4,4,5,5-pentafluoro-1-((2-((-4,4,4-trifluoro-3-oxobut-1-en-1-yl)amino)phenyl)amino)pent-1-en-3-one was obtained. APCI-MS (positive): 581.8 $[M+H]^+$.

1-(3-Chloro-4-(trifluoromethyl)phenyl)-4,4,5,5-pentafluoro-1-((2-((-4,4,4-trifluoro-3-oxobut-1-en-1-yl)amino)phenyl)amino)pent-1-en-3-one (1.9 g, 3.2 mmol) was added to a solution of cerium(IV) isopropoxide (0.32M in DME/iPrOH, 1.63 mmol, 5.1 ml). Hexane was added and the resulting solid was filtered off and washed with hexane. The residue was dissolved in chloroform, filtered, and recrystallized from chloroform/hexane. A red solid (9), 0.41 g (0.316 mmol, 20%) was obtained. APCI-MS (positive): 1296.8 $[M+H]^+$.

The metal complex (9) (313 mg) was sublimed at 180-190 °C at $3 \cdot 10^{-6}$ mbar. The yield was 167 mg (53%). The metal complex (9) decomposes at 244 °C.

Cyclic voltammetry of 9 in acetonitrile (ACN, 200 mV/s, 0.1M $NBu_4PF_6$) resulted in the following: $E_{1/2}$ (vs. Fc/$Fc^+$)=+0.0V.

When ZnPc (zinc phthalocyanine) was doped with 20 wt % of the dopant (9), an increase in conductivity up to $1.1 \cdot 10^{-5}$ S/cm was measured after co-evaporation in vacuum. The intrinsic conductivity of ZnPc without doping is $<1 \cdot 10^{-8}$ S/cm. (Tietze, M. L., Pahner, P., Schmidt, K., Leo, K., & Lüssem, B. (2015). *Advanced Functional Materials,* 25(18), 2701-2707).

When spiro-MeO-TAD (CAS No.: 207739-72-8) was doped with 20 wt % of dopant (9), an increase in conductivity up to 5.1.10-6 S/cm was measured after solvent processing (spin coating). The intrinsic conductivity of the spiro-MeO-TAD without doping was measured to be $2 \cdot 10^{-8}$ S/cm.

The invention claimed is:

1. A compound of general formula $$Ce^{4+}[L_1L_2]^{4-} \quad (I),$$

their charge transfer complexes, their reduction products and mixtures thereof, wherein $L_1$ and $L_2$ are each a tetradentate ligand independently selected from ligands of formula (I.1)

(I.1)

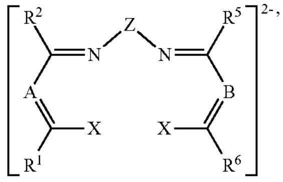

wherein

X independently from each other represents O or S;

Z is a bridging group, which has 2 or 3 carbon atoms between the nitrogen atoms, wherein the carbon atoms each being unsubstituted or substituted by 1, 2, 3, 4, 5 or 6 identical or different radicals $R^{12}$, wherein two adjacent carbon atoms may be linked to one another by a double bond, or 2 or 3 of the carbon atoms are part of a mononuclear, 2-nuclear or 3-nuclear $C_6$-$C_{14}$ aromatic or heteroaromatic ring system, wherein the heteroaromatic ring system has 4 to 13 carbon atoms and has 1, 2 or 3 identical or different heteroatoms or heteroatom-containing groups as ring members selected from N, $NR^8$, O, S, SO and $SO_2$ and wherein the aromatic or heteroaromatic ring system is unsubstituted or substituted by 1, 2, 3, 4 or 5 identical or different radicals $R^9$;

A and B independently from each other represent N or $CR^7$;

$R^1$ and $R^6$ are independently selected from hydrogen, CN, $C_1$-$C_6$ alkyl, $C_1$-$C_6$ haloalkyl, $C_1$-$C_6$ alkoxy, $C_1$-$C_6$ haloalkoxy, $C_3$-$C_7$ cycloalkyl, wherein $C_3$-$C_7$-cycloalkyl is unsubstituted or substituted by 1, 2, 3, 4, 5 or 6 identical or different radicals $R^{11}$, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$; or $R^1$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^6$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^2$ and $R^5$ are independently selected from hydrogen, CN, $C_1$-$C_6$ alkyl, $C_1$-$C_6$ haloalkyl, $C_1$-$C_6$ alkoxy, $C_1$-$C_6$ haloalkoxy, $C_3$-$C_7$ cycloalkyl, wherein $C_3$-$C_7$ cycloalkyl is unsubstituted or substituted by 1, 2, 3, 4, 5 or 6 identical or different radicals $R^{11}$, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

$R^2$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^5$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^{4a}R^{4b}$ are independently from each other selected from hydrogen, $C_1$-$C_6$ alkyl and $C_6$-$C_{14}$ aryl, wherein aryl is unsubstituted or substituted with 1, 2, 3, 4 or 5 identical or different radicals $R^{10}$;

$R^7$ is selected from hydrogen, CN, nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl has 1, 2 or 3 identical or different heteroatoms or heteroatom-containing groups as ring members selected from N, $NR^8$, O, S, SO and $SO_2$, wherein aryl and hetaryl are unsubstituted or substituted with 1, 2, 3, 4 or 5 identical or different radicals $R^{10}$;

$R^8$ is selected from hydrogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl;

$R^{10}$ is selected from CN, halogen, $C_1$-$C_4$ alkyl, $C_1$-$C_4$ haloalkyl;

$R^{11}$ is selected from CN, halogen, $C_1$-$C_4$ alkyl, $C_1$-$C_4$ haloalkyl;

$R^{12}$ independently selected from halogen, CN, $C_1$-$C_6$ alkyl, $C_1$-$C_6$ haloalkyl, $C_1$-$C_6$ alkoxy, $C_1$-$C_6$ haloalkoxy, $C_3$-$C_7$ cycloalkyl, where $C_3$-$C_7$ cycloalkyl is unsubstituted or substituted by 1, 2, 3, 4, 5 or 6 identical or different radicals $R^{11}$, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

with the proviso that the following compounds are excluded:

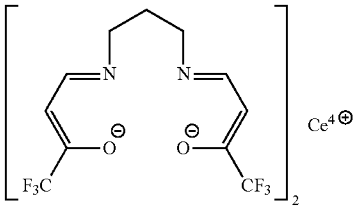

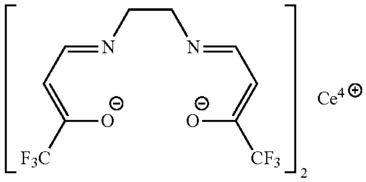

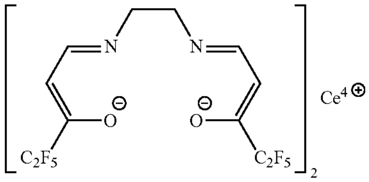

-continued

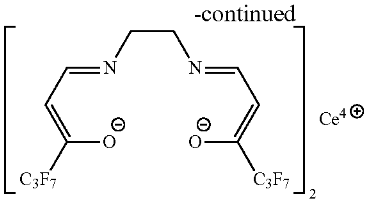

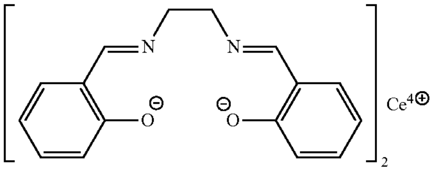

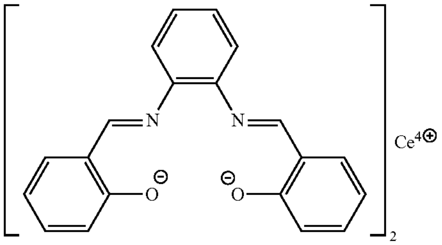

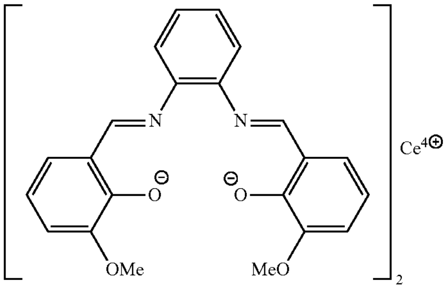

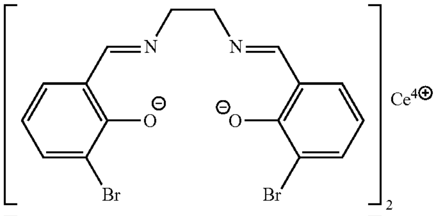

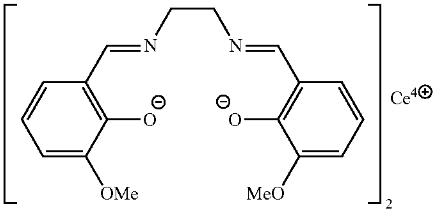

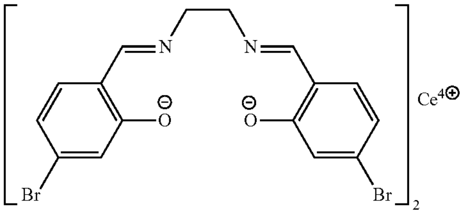

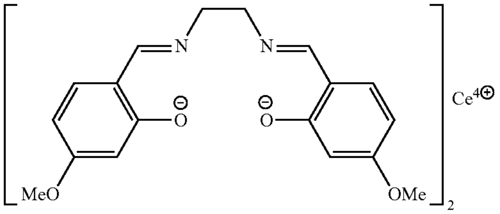

-continued

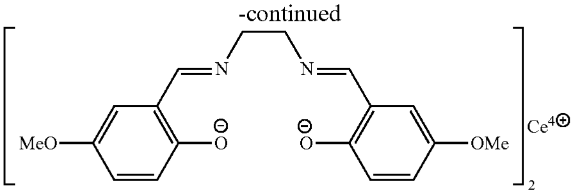

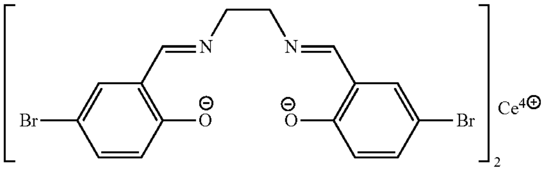

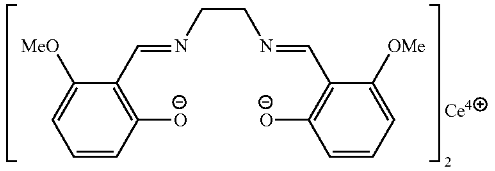

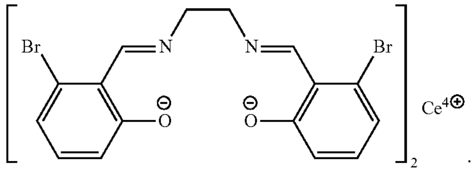

2. The compounds of general formula (I) according to claim 1

$$Ce^{4+}[L_1L_2]^{4-} \quad (I),$$

their charge transfer complexes, their reduction products and mixtures thereof, wherein $L_1$ and $L_2$ are each a tetradentate ligand independently selected from ligands of formula (II)

(II)

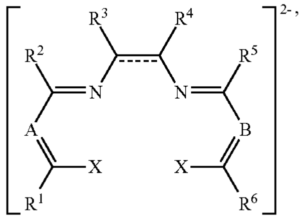

wherein

------ between the group $CR^3$—$CR^4$ represents a single or double bond;

X independently from each other represents O or S;

A and B independently from each other represent N or $CR^7$;

$R^1$ and $R^6$ are independently selected from hydrogen, CN, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$; or $R^1$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^6$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^3$ and $R^4$ are independently selected from hydrogen, CN, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$, or $R^3$ and $R^4$ together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different $R^9$ radicals;

$R^2$ and $R^5$ are independently selected from hydrogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

$R^{4a}R^{4b}$ are independently from each other selected from hydrogen, $C_1$-$C_6$ alkyl and $C_6$ $C_{14}$ aryl, wherein aryl is unsubstituted or substituted with 1, 2, 3, 4 or 5 identical or different radicals $R^{10}$;

$R^7$ is selected from hydrogen, CN, nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl has 1, 2 or 3 identical or different heteroatoms or heteroatom-containing groups as ring members selected from N, $NR^8$, O, S, SO and $SO_2$, wherein aryl and hetaryl are unsubstituted or substituted with 1, 2, 3, 4 or 5 identical or different radicals $R^{10}$;

$R^8$ is selected from hydrogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl;

$R^{10}$ is selected from CN, halogen, $C_1$-$C_4$ alkyl, $C_1$-$C_4$ haloalkyl, with the proviso that the following compounds and their reaction products of formula (I) are excluded:

$L_1$=$L_2$=N,N'-bis(4,4,4,-trifluorobut-1-en-3-one)-ethylendiamine, $L_1$=$L_2$=N,N'-bis(4,4,5,5,5-pentafluoropent-1-en-3-one)-ethylendiamine, $L_1$=$L_2$=N,N'-bis(4,4,5,5,6,6,6-heptafluorohex-1-en-3-one)-ethylendiamine and the following compounds and their reaction products:

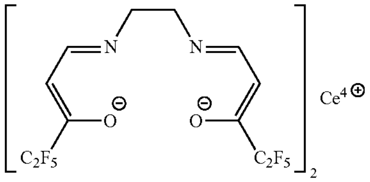

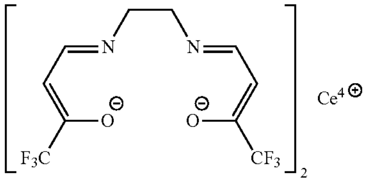

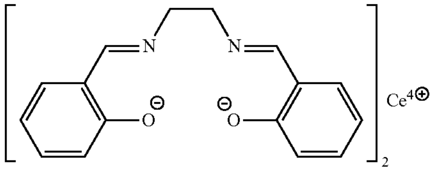

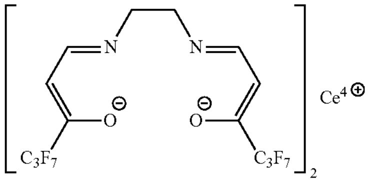

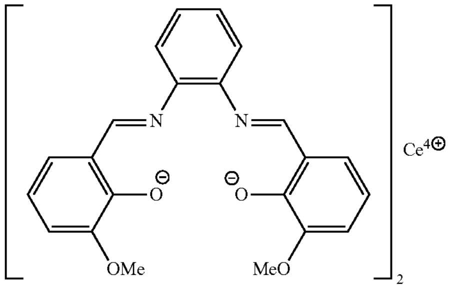

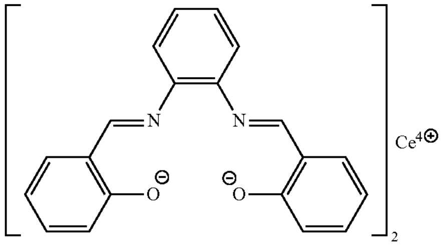

-continued

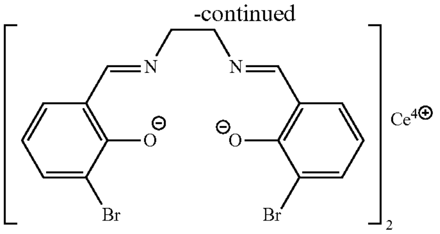

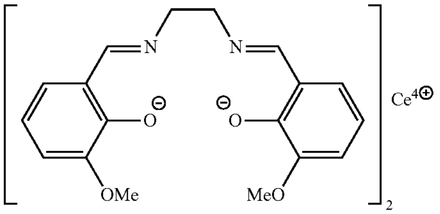

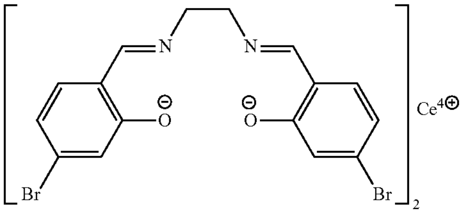

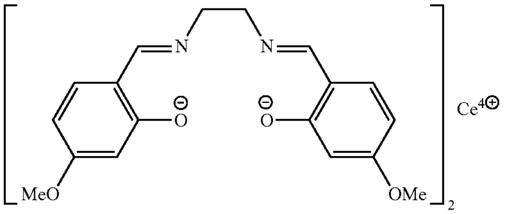

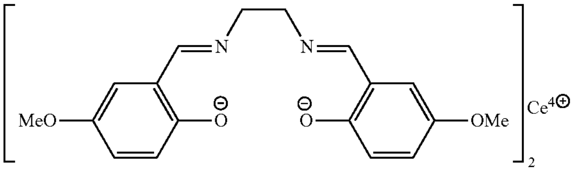

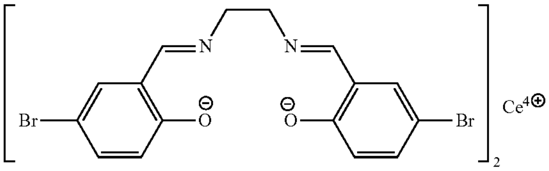

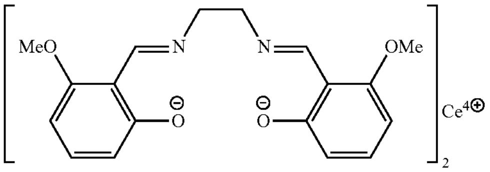

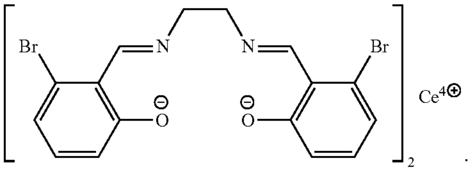

.

3. An electronic component comprising at least one compound of claim 1.

4. The electronic component according to claim 3, wherein $L_1$ and $L_2$ are each a tetradentate ligand independently selected from ligands of formula (II)

(II)

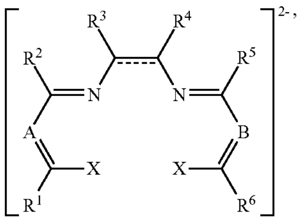

wherein between the group $CR^3$—$CR^4$ represents a single or double bond;

X independently from each other represents O or S;

A and B independently from each other represent N or $CR^7$;

$R^1$ and $R^6$ are independently selected from hydrogen, CN, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$; or $R^1$ and A together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$, or $R^6$ and B together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different radicals $R^9$;

$R^3$ and $R^4$ are independently selected from hydrogen, CN, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$, or $R^3$ and $R^4$ together with the carbon atom to which they are attached form a $C_6$-$C_{14}$ aryl group or hetaryl group having 4 to 13 carbon atoms, wherein hetaryl having 1, 2 or 3 identical or different heteroatoms or heteroatom-containing groups as ring members selected from N, $NR^8$, O, S, SO and $SO_2$, aryl and hetaryl being unsubstituted or substituted with 1, 2, 3 or 4 identical or different $R^9$ radicals;

$R^2$ and $R^5$ are independently selected from hydrogen, CN, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl having 1, 2 or 3 identical or different heteroatoms or heteroatom-containing groups as ring members selected from N, $NR^8$, O, S, SO and $SO_2$, wherein aryl and hetaryl being unsubstituted or substituted with 1, 2, 3, 4 or 5 identical or different radicals $R^9$;

$R^{4a}$ and $R^{4b}$ are independently from each other selected from hydrogen, $C_1$-$C_6$ alkyl and $C_6$-$C_{14}$ aryl, wherein aryl is unsubstituted or substituted with 1, 2, 3, 4 or 5 identical or different radicals $R^{10}$;

$R^7$ is selected from hydrogen, CN, nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$, $C_6$-$C_{14}$ aryl and hetaryl having 4 to 13 carbon atoms, wherein hetaryl has 1, 2 or 3 identical or different heteroatoms or heteroatom-containing groups as ring members selected from N, $NR^8$, O, S, SO and $SO_2$, wherein aryl and hetaryl are unsubstituted or substituted with 1, 2, 3, 4 or 5 identical or different radicals $R^{10}$;

$R^8$ is selected from hydrogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl;

$R^{10}$ is selected from CN, halogen, $C_1$-$C_4$ alkyl, $C_1$-$C_4$ haloalkyl.

5. The electronic component according to claim 3, wherein in formula (I.1) $R^1$, $R^2$, $R^5$ and $R^6$ are independently selected from hydrogen, CN, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylsulfanyl, $C_1$-$C_6$ haloalkylsulfanyl, $NR^{4a}R^{4b}$ and group A consisting of A1, A2, A3, A4, A5, A6, A7, A8, A9, A10, A11, A12, A13, A14, A15, A16, A17, A18 and A19

A 1

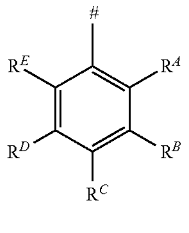

A 2

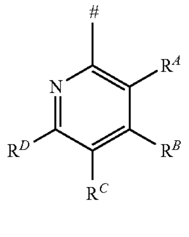

-continued
A 3
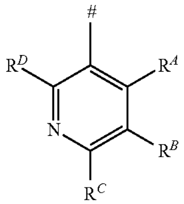
A 4
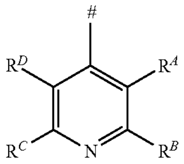
A 5
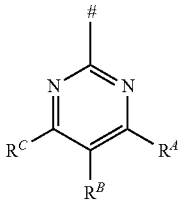
A 6
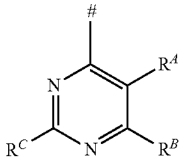
A 7
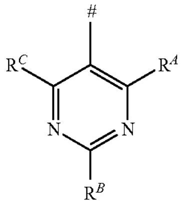
A 8
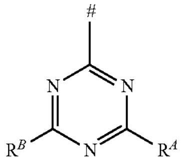
A 9
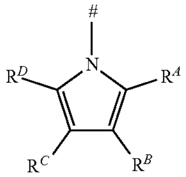
A 10
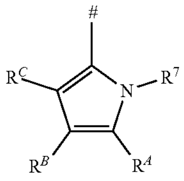
-continued
A 11
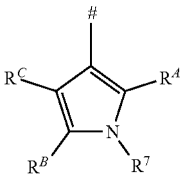
A 12
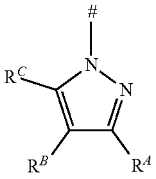
A 13
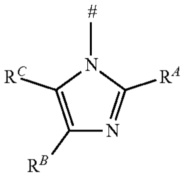
A 14
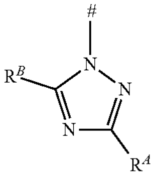
A 15
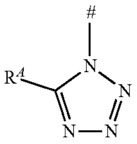
A 16
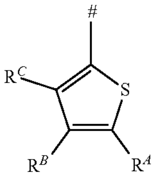
A 17
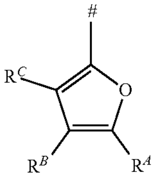
A 18
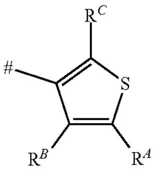

-continued

A 19

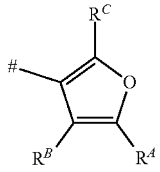

wherein # denotes the bond to the group of formula (I) wherein $R^A$, $R^B$, $R^C$, $R^D$ and $R^E$ are independently selected from hydrogen, CN, halogen, $C_1$-$C_4$ alkyl and $C_1$-$C_4$ haloalkyl; or $R^1$ and A together with the carbon atom to which they are attached form a $C_6$-$C_{14}$ aryl group, wherein aryl is unsubstituted or substituted with 1, 2, 3 or 4 identical or different radicals $R^9$; or $R^6$ and B together with the carbon atom to which they are attached form a $C_6$-$C_{14}$ aryl group, wherein aryl is unsubstituted or substituted with 1, 2, 3 or 4 identical or different radicals $R^9$;

$R^{4a}$, $R^{4b}$ are independently selected from hydrogen, $C_1$-$C_6$ alkyl and $C_6$-$C_{14}$ aryl, wherein aryl is unsubstituted or substituted with 1, 2, 3, 4 or 5 identical or different radicals $R^{10}$;

$R^9$ is selected from CN, halogen, $C_1$-$C_6$ alkyl, $C_1$-$C_6$ haloalkyl and $C_6$-$C_{14}$ aryl, wherein aryl is unsubstituted or substituted with 1, 2, 3, 4 or 5 identical or different radicals selected from $C_1$-$C_4$ alkyl and $C_1$-$C_4$ haloalkyl; and $R^{10}$ is selected from CN, halogen, $C_1$-$C_4$ alkyl and $C_1$-$C_4$ haloalkyl.

6. The electronic component according to claim 4, wherein in formula (II) $R^3$ and $R^4$ are independently selected from hydrogen, CN, $C_1$-$C_6$ alkyl, $C_1$-$C_6$ haloalkyl, $C_1$-$C_6$ alkoxy and $C_1$-$C_6$ haloalkoxy and phenyl, wherein phenyl is unsubstituted or substituted by 1, 2, 3 or 4 identical or different radicals $R^9$, or $R^3$ and $R^4$ together with the carbon atoms to which they are attached form a $C_6$-$C_{14}$ aryl group wherein aryl is unsubstituted or substituted with 1, 2, 3 or 4 identical or different radicals $R^9$;

$R^9$ is selected from CN, halogen, $C_1$-$C_6$ alkyl, $C_1$-$C_6$ haloalkyl or $C_6$-$C_{14}$ aryl, wherein aryl is unsubstituted or substituted with 1, 2, 3, 4 or 5 identical or different substituents selected from $C_1$-$C_4$ alkyl or $C_1$-$C_4$ haloalkyl.

7. The electronic component according to claim 3, wherein in formula (1.1) A and B are independently a radical $CR^7$ and $R^7$ is selected from hydrogen, CN, nitro, halogen and group B consisting of B1, B2, B3, B4, B5, B6, B7, B8, B9, B10, B11, B12, B13, B14 and B15

B 1

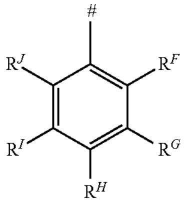

-continued

B 2

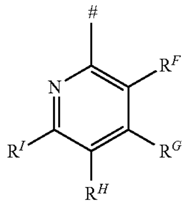

B 3

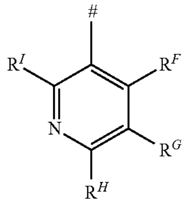

B 4

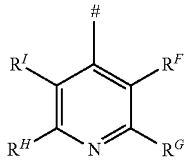

B 5

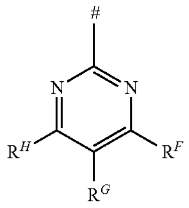

B 6

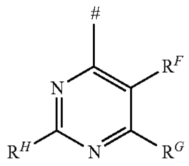

B 7

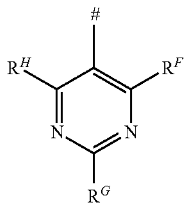

B 8

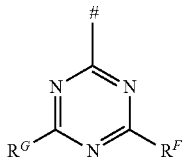

B 9

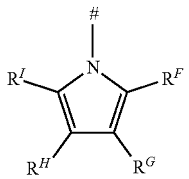

-continued

B 10

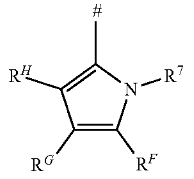

B 11

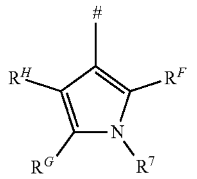

B 12

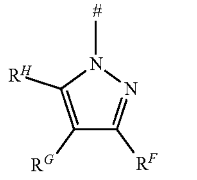

B 13

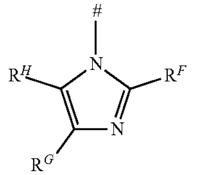

B 14

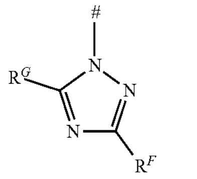

B 15

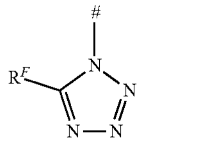

wherein # denotes the bond to the group of formula (1.1), and wherein $R^F$, $R^G$, $R^H$, $R^I$ and $R^J$ are independently selected from hydrogen, CN, halogen, $C_1$-$C_4$ alkyl and $C_1$-$C_4$ haloalkyl.

8. The electronic component according to claim 3, wherein in $R^1$, $R^2$, $R^5$ and $R^6$, in formula (1.1), A and B are independently selected from hydrogen, $C_1$-$C_4$ alkyl, $C_1$-$C_4$ haloalkyl, and A1

A1

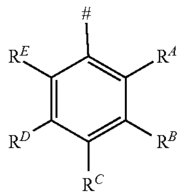

# denotes the bond to the remaining molecule of formula (1.1), and wherein $R^A$, $R^B$, $R^C$, $R^D$ and $R^E$ are independently selected from hydrogen, CN, fluorine, chlorine, $C_1$-$C_4$ alkyl, $C_1$-$C_4$ fluoroalkyl and $C_1$-$C_4$ chloroalkyl, preferably selected from hydrogen, CN, fluorine and chlorine; or $R^1$ and A together with the carbon atom to which they are attached form a phenyl ring, wherein phenyl is unsubstituted or substituted with 1, 2, 3 or 4 identical or different radicals $R^9$; or $R^6$ and B together with the carbon atom to which they are attached form a phenyl ring, wherein phenyl is unsubstituted or substituted with 1, 2, 3 or 4 identical or different radicals $R^9$;

$R^9$ is selected from CN, halogen, $C_1$-$C_4$ alkyl, $C_1$-$C_4$ haloalkyl and phenyl, wherein phenyl is unsubstituted or substituted with 1, 2, 3, 4 or 5 identical or different substituents selected from $C_1$-$C_4$ alkyl or $C_1$-$C_4$ haloalkyl.

9. The electronic component according claim 3, wherein in formula (1.1) A and B are independently a radical $CR^7$ and $R^7$ is selected from hydrogen, CN, nitro, halogen, $C_1$-$C_2$ alkyl and $C_1$-$C_2$ haloalkyl.

10. The electronic component according to claim 3, wherein $R^3$ and $R^4$ are selected independently of one another from hydrogen, CN, $C_1$-$C_4$-alkyl, $C_1$-$C_4$-haloalkyl, or $R^3$ and $R^4$ together with the carbon atoms to which they are attached form a phenyl ring, wherein phenyl is unsubstituted or substituted by 1, 2, 3 or 4 identical or different radicals $R^9$;

$R^9$ is selected from CN, halogen, $C_1$-$C_4$-alkyl, $C_1$-$C_4$-haloalkyl or phenyl, where phenyl is unsubstituted or substituted by 1, 2, 3 or 4 identical or different substituents selected from $C_1$-$C_4$-alkyl or $C_1$-$C_4$-haloalkyl.

11. The electronic component according to claim 3, wherein $L_1$ and $L_2$ have the same meanings.

12. The electronic component according to claim 3, in the form of an organic light-emitting diode, an organic solar cell, a photovoltaic cell, an organic sensor, an organic diode or an organic field-effect transistor, preferably in form of a thin-film transistor.

13. The electronic component according to claim 3, having a layer structure, which comprises 2, 3, 4, 5, 6, 7 or more layers.

14. The electronic component according to claim 3, comprising a hole transport layer and/or a hole injection layer, which comprises at least the compound of formula (I).

15. The electronic component according to claim 3, comprising an electron transport layer, which comprises at least of the compound of formula (I).

16. Doped semiconductor matrix material comprising at least one electron donor and at least one compound of the formula (I) as defined in claim 1, wherein the electron donor is preferably selected from 4,4',4"-tris(N-(2-naphthyl)-N-phenyl-amino)triphenylamine (2-TNATA), 4,4',4"-tris(N-3-methylphenyl-N-phenyl-amino)triphenylamine (m-MTDATA), N,N,N',N'-tetrakis(4-methoxy-phenyl)benzidine (MeO-TPD), (2,2',7,7'-tetrakis-(N,N-diphenylamino)-9,9'-spirobifluorene (spiro-TTB), N,N'-bis(naphthalene-1-yl)-N,N'-bis(phenyl)-benzidine, N,N'-bis(naphthalene-1-yl)-N,N'-bis(phenyl)-9,9-spiro-bifluorene, 9,9-bis[4-(N, N-bis-biphenyl-4-yl-amino)phenyl]-9H-fluorene, 2,2'-bis[N,N-bis (biphenyl-4-yl)amino]-9,9-spiro-bifluorene, N,N'-((9H-fluorene-9,9-diyl)bis(4,1-phenylene))bis(N-([1,1'-biphenyl]-4-yl)-[1,1'-biphenyl]-4-amine) (BPAPF), N,N'-bis (phenanthrene-9-yl)-N,N'-bis(phenyl)-benzidine, 1,3,5-tris {4-[bis(9,9-dimethyl-fluorene-2-yl)amino] phenyl} benzene, tri (terphenyl-4-yl)amine, N-(4-(6-((9,9-dimethyl-9H-fluorene-2-yl) (6-methoxy-[1,1'-biphenyl]-3-yl)amino)-1,3,3-trimethyl-2,3-dihydro-1H-indene-1-yl)phenyl)-N-(6-methoxy-[1,1'-biphenyl]-3-yl)-9,9-dimethyl-9H-fluorene-2-amine, N-([1,1'-biphenyl]-4-yl)-N-(4-(6-([1,1'-biphenyl]-4-yl(9,9-dimethyl-9H-fluorene-2-yl)amino)-1,3,3-trimethyl-2,3-dihydro-1H-indene-1-yl)phenyl)-9,9-dimethyl-9H-fluorene-2-amine, N, N-di([1,1'-biphenyl]-4-yl)-3-(4-(di([1,1'-biphenyl]-4-yl)amino)phenyl)-1,1,3-trimethyl-2,3-dihydro-1H-indene-5-amine, N-(4-(6-(bis(9,9-dimethyl-9H-fluorene-2-yl)amino)-1,3,3-trimethyl-2,3-dihydro-1H-inden-1-yl)phenyl)-N-(9,9-dimethyl-9H-fluorene-2-yl)-9,9-dimethyl-9H-fluorene-2-amine, N-(4-(6-(9,9'-spirobi[fluorene]-2-yl(9,9-dimethyl-9H-fluorene-2-yl)amino)-1,3,3-trimethyl-2,3-dihydro-1H-inden-1-yl)phenyl)-N-(9,9-dimethyl-9H-fluoren-2-yl)-9,9'-spirobi[fluorene]-2-amine, N-(4-(6-(dibenzo[b,d]furane-2-yl(9,9-dimethyl-9H-fluorene-2-yl)amino)-1,3,3-trimethyl-2,3-dihydro-1H-indene-1-yl)-phenyl)-N-(9,9-dimethyl-9H-fluorene-2-yl)dibenzo[b,d]furan-2-amine, 9-(4-(6-(9H-carbazol-9-yl)-1,3,3-trimethyl-2,3-dihydro-1H-inden-1-yl)phenyl)-9H-carbazole, N-([1,1'-biphenyl]-4-yl)-3-(4-([1,1'-biphenyl]-4-yl(4-methoxyphenyl)amino)phenyl)-N-(4-methoxyphenyl)-1,1,3-trimethyl-2,3-dihydro-1H-inden-5-amine, 3-(4-(bis(6-methoxy-[1,1'-biphenyl]-3-yl)amino)phenyl)-N, N-bis(6-methoxy-[1,1'-biphenyl]-3-yl)-1,1,3-trimethyl-2,3-dihydro-1H-indene-5-amine, N1-([1,1'-biphenyl]-4-yl)-N1-(4-(6-([1,1'-biphenyl]-4-yl(4-(diphenylamino)phenyl) amino)-1,3,3-trimethyl-2,3-dihydro-1H-inden-1-yl)phenyl)-N4,N4-diphenylbenzene-1,4-diamine, N,N-di([1,1'-biphenyl]-4-yl)-4'-(6-(4-(di([1,1'-biphenyl]-4-yl)amino)phenyl)-1,3,3-trimethyl-2,3-dihydro-1H-indene-1-yl)-[1,1'-biphenyl]-4-amine, N-(4-(5-(bis(9,9-dimethyl-9H-fluorene-2-yl)amino)-1,3,3-trimethyl-2,3-dihydro-1H-indene-1-yl)phenyl)-N-(9,9-dimethyl-9H-fluorene-2-yl)-9,9-dimethyl-9H-fluorene-2-amine, N-(4-(6-(bis(9,9-dimethyl-9H-fluorene-2-yl)amino)-1,3,3-trimethyl-2,3-dihydro-1H-indene-1-yl)-phenyl)-N-(9,9-dimethyl-9H-fluorene-2-yl)-9,9-dimethyl-9H-fluorene-2-amine, N,N'-bis(9,9-dimethyl-fluorene-2-yl)-N,N'-diphenyl-benzidine (BF-DPB), N,N'-((9H-fluorene-9,9-diyl)bis(4,1-phenylene))bis(N-([1,1'-biphenyl]-4-yl)-[1,1'-biphenyl]-4-amine) (BPAPF), N4,N4,N4', N4'-tetrakis(9,9-dimethyl-9H-fluorene-2-yl)-[1,1'-biphenyl]-4,4'-diamine (TDMFB), N-([1,1'-biphenyl]-2-yl)-N-(9,9-dimethyl-9H-fluorene-2-yl)-9,9'-spirobi[fluorene]-2-amine, (2,7-bis[N,N-bis(4-methoxyphenyl)amino]-9,9-spirobi[9H-fluorene] (spiro-MeO-TPD), a mixture of N-(4-(5-(bis(9,9-dimethyl-9H-fluorene-2-yl)amino)-1,3,3-trimethyl-2,3-dihydro-1H-inden-1-yl)phenyl)-N-(9,9-dimethyl-9H-fluorene-2-yl)-9,9-dimethyl-9H-fluorene-2-amine and N-(4-(6-(bis(9,9-dimethyl-9H-fluorene-2-yl)amino)-1,3,3-trimethyl-2,3-dihydro-1H-inden-1-yl)phenyl)-N-(9,9-dimethyl-9H-fluorene-2-yl)-9,9-dimethyl-9H-fluorene-2-amine, N-([1,1'-biphenyl]-4-yl)-9,9-dimethyl-N-(4-(9-phenyl-9H-carbazol-3-yl)phenyl)-9H-fluorene-2-amine and mixtures thereof.

17. A method for the production of an organic semiconductor, a doping agent in organic semiconductor matrix materials, especially as p-dopant in hole transport layers, a charge injector in a charge injection layer, an electron transport layer, a cathode material in organic batteries, an electrochromic material an electron acceptor, wherein a compound of formula (I) or mixtures thereof, as defined in claim 1 is employed.

* * * * *